(12) United States Patent
Cintas et al.

(10) Patent No.: US 12,299,564 B2
(45) Date of Patent: May 13, 2025

(54) PATTERN DISCOVERY, PREDICTION AND CAUSAL EFFECT ESTIMATION IN TREATMENT DISCONTINUATION

(71) Applicant: International Business Machines Corporation, Armonk, NY (US)

(72) Inventors: Celia Cintas, Nairobi (KE); Victor Abayomi Akinwande, Karen (KE); Aisha Walcott, Nairobi (KE); Ramya Raghavendra, New York, NY (US); Komminist Weldemariam, Ottawa (CA)

(73) Assignee: International Business Machines Corporation, Armonk, NY (US)

( * ) Notice: Subject to any disclaimer, the term of this patent is extended or adjusted under 35 U.S.C. 154(b) by 1176 days.

(21) Appl. No.: 17/133,285

(22) Filed: Dec. 23, 2020

(65) Prior Publication Data
US 2022/0198265 A1    Jun. 23, 2022

(51) Int. Cl.
  *G06N 3/08*  (2023.01)
  *G06F 18/21*  (2023.01)
  (Continued)

(52) U.S. Cl.
  CPC ........... *G06N 3/08* (2013.01); *G06F 18/2132* (2023.01); *G06F 18/217* (2023.01); *G06F 18/40* (2023.01);
  (Continued)

(58) Field of Classification Search
  CPC .......... G06N 3/08; G06N 3/044; G16H 20/00; G06F 18/2132; G06F 18/217; G06F 18/40
  See application file for complete search history.

(56) References Cited

U.S. PATENT DOCUMENTS 8,543,215 B2    9/2013  Hatlestad
11,631,484 B1*  4/2023  Hanina .................. G16H 80/00
                                                  706/11
(Continued)

FOREIGN PATENT DOCUMENTS

CA    2789885 A1    3/2014
CN    204520641     8/2015

OTHER PUBLICATIONS

Maharajan et al., "A Tutorial Markov Analysis of Effective Human Tutorial Sessions," Proceedings of the 5th Workshop on Natural Language Processing Techniques for Education Applications, pp. 30-34 Melbourne, Australia, Jul. 19, 2018 (Year: 2018).*

(Continued)

*Primary Examiner* — Shahid K Khan
(74) *Attorney, Agent, or Firm* — Shimon Benjamin; Otterstedt & Kammer PLLC

(57) ABSTRACT

With a trained, computerized discontinuation predictor machine learning component (MLC), predict, based on an input time series, a time when a subject will discontinue a course of medical treatment; with a trained, computerized pattern behavior extractor MLC, extract from said input time series the top k discriminatory sequences via discriminatory sub-sequence mining (said top k discriminatory sequences differentiate between first and second classes of interest to provide a hypothesis for downstream analysis of a cause of discontinuing said course of treatment). With a trained, causal effect estimator computerized MLC, determine a reason why said subject will discontinue said course of medical treatment, based on said top k discriminatory sequences and additional data; and with a computerized user interface, provide said time and said reason why to a responsible party to initiate an intervention.

20 Claims, 17 Drawing Sheets

(51) Int. Cl.
  G06F 18/2132   (2023.01)
  G06F 18/40    (2023.01)
  G06N 3/044    (2023.01)
  G16H 20/00    (2018.01)
  G16H 50/20    (2018.01)
  G16H 50/70    (2018.01)
(52) U.S. Cl.
  CPC ............ *G06N 3/044* (2023.01); *G16H 20/00* (2018.01); *G16H 50/20* (2018.01); *G16H 50/70* (2018.01)

(56) References Cited

U.S. PATENT DOCUMENTS

| | | | | |
|---|---|---|---|---|
| 2004/0210117 | A1* | 10/2004 | Ueno | G16H 70/00 |
| | | | | 128/920 |
| 2013/0006671 | A1* | 1/2013 | Hufford | G16H 10/20 |
| | | | | 705/3 |
| 2014/0310016 | A1 | 10/2014 | Kenney | |
| 2017/0277835 | A1 | 9/2017 | Bell | |
| 2021/0241137 | A1* | 8/2021 | Jain | G16H 10/20 |

OTHER PUBLICATIONS

Abhar, Orhan, "Rule Mining and Sequential Pattern Based Predictive Modeling with EMR Data" (2019) Theses and Dissertations—Computer Science 85 (Year: 2019).*
Fournier-Viger, Philippe, and Vincent S. Tseng, "Mining top-k sequential rules," International Conference on Advanced Data Mining and Applications, Berlin, Heidelberg: Springer Berlin Heidelberg, 2011 (Year: 2011).*
Brownlee, Jason, "4 Types of Classification Tasks in Machine Learning" (Apr. 8, 2020) (Year: 2020).*
Faraone, Stephen V., "Interpreting Estimates of Treatment Effects" (Dec. 2008) P&T 2008 vol. 33, No. 12 (Year: 2008).*
Azuike et al., Predictors of discontinuation of contraceptive use among Nigerian women: Results of 2013 Nigeria Demographic and Health Surveys, Journal of Scientific Research and Studies vol. 4 (7), pp. 171-176, Jul. 2017.
Bradley et al., "Levels, Trends, and Reasons for Contraceptive Discontinuation", US Aid From the Amercian People, DHS Analytical Studies 20, ICF Macro, Calverton, Maryland, USA, Sep. 2009, 109 pages.
Emam et al., "Predicting the Long-Term Outcomes of Biologics in Psoriasis Patients Using Machine Learning", Submitted on Aug. 25, 2019, arXiv:1908.09251, pp. 1-14.
Wang et al., "Contraceptive Discontinuation, Failure, and Switching in Cambodia", Further Analysis of the 2014 Cambodia Demographic and Health Survey, DHS Further Analysis Reports No. 105, ICF, Rockville, Maryland, USA, 34 pages.
IBM Releases SQL-Native Time Series Processing in Cloud. Downloaded from https://www.ibm.com/blog/announcement/ibm-releases-sql-native-time-series-processing-in-cloud/ Nov. 26, 2020. pp. 6.
Horvitz-Thompson estimator. Downloaded from https://en.wikipedia.org/wiki/Horvitz%E2%80%93Thompson_estimator Nov. 26, 2020. pp. 2.
Rosenbaum, Paul R, Constructing a Control Group Using Multivariate Matched Sampling Methods That Incorporate the Propensity Score. The American Statistician vol. 39, No. 1 (Feb. 1985), pp. 33-38 (6 pages).
The DHS Program—Calendar Tutorial. pp. 2.
Gesesew HA, Ward P, Hajito KW, Feyissa GT, Mohammadi L, Mwanri L. Discontinuation from antiretroviral therapy: a continuing challenge among adults in HIV care in Ethiopia: a systematic review and meta-analysis. PloS one. Jan. 20, 2017;12(1):e0169651.
Ann K Blanc, Sian L Curtis, and Trevor N Croft. Monitoring contraceptive continuation: links to fertility outcomes and quality of care. Studies in family planning, 33(2):127-140, 2002.
Sian L Curtis, Ian Diamond, and John W McDonald. Birth interval and family effects on postneonatal mortality in brazil. Demography, 30(1):33-43, 1993.
Annet Nanvubya, Julius Ssempiira, Juliet Mpendo, Ali Ssetaala, Annet Nalutaaya, Mathias Wambuzi, Paul Kitandwe, Bernard S Bagaya, Sabrina Welsh, Stephen Asiimwe, et al. Use of modern family planning methods in fishing communities of lake victoria, uganda. PloS one, 10(10), 2015.
Kerry L. D. MacQuarrie, Christina Juan, Courtney Allen, Sally Zweimueller, and Alison Gemmill. Women's contraceptive profiles throughout the life course in burundi and nepal. Technical report, DHS Analytical Studies No. 72, 2019.
Jian Pei et al,. Mining Sequential Patterns by Pattern-Growth: The PrefixSpan Approach. IEEE Transactions on Knowledge and Data Engineering, vol. 16, No. 10, Oct. 2004. pp. 17.
Mohammed J Zaki. Spade: An efficient algorithm for mining frequent sequences. Machine learning, 42(1-2):31-60, 2001.
Miguel A Hern'an and James M Robins. Estimating causal effects from epidemiological data. Journal of Epidemiology & Community Health, 60(7):578-586, 2006.
Paul R Rosenbaum and Donald B Rubin. The central role of the propensity score in observational studies for causal effects. Biometrika, 70(1):41-55, 1983.
David W Scott. Multivariate density estimation: theory, practice, and visualization. John Wiley & Sons, 2015.
Susan Athey and Guido Imbens. Recursive partitioning for heterogeneous causal effects. Proceedings of the National Academy of Sciences, 113(27):7353-7360, 2016.
Mshai Shimoni, Ehud Karavani, Sivan Ravid, Peter Bak, Tan Hung Ng, Sharon Hensley Alford, Denise Meade, and Yaara Goldschmidt. An evaluation toolkit to guide model selection and cohort definition in causal inference. arXiv preprint arXiv:1906.00442, 2019.
Richard K Crump, V Joseph Hotz, Guido W Imbens, and Oscar A Mitnik. Dealing with limited overlap in estimation of average treatment effects. Biometrika, 96(1):187-199, 2009.
Fredrik D Johansson, Dennis Wei, Michael Oberst, Tian Gao, Gabriel Brat, David Sontag, and Kush R Varshney. Characterization of overlap in observational studies. arXiv preprint arXiv:1907.04138, 2019.
Ehud Karavani, Peter Bak, and Yishai Shimoni. A discriminative approach for finding and characterizing positivity violations using decision trees. arXiv preprint arXiv:1907.08127, 2019.
Johns Hopkins Bloomberg School of Public Health. PMA: Performance Monitoring for Action. https://www.pmadata.org/, 2019.
Finale Doshi-Velez and Been Kim. Towards a rigorous science of interpretable machine learning. arXiv preprint arXiv:1702.08608, 2017.

* cited by examiner

| Subsequence | Supp. Left | Supp. Right | Lift |
|---|---|---|---|
| 3 → 0 | 0.33125 | 0.00909 | 36.429 |
| 3 → 3 → 3 → 0 | 0.33644 | 0.00005 | 561.28 |
| 3 → 3 → 0 → 0 | 0.34579 | 0.00005 | 663.40 |
| 3 → 3 → 0 → 0 | 0.33888 | 0.10357 | 3.2715 |
| 3 → 3 → 0 → 0 → 0 | 0.31896 | 0.14345 | 2.2233 |
| 3 → 3, → 3 → 3 → 0 | 0.30508 | 0.27232 | 1.1203 |

*FIG. 3*

| Person_id | Timestamp | Episode | Discontinuation |
|---|---|---|---|
| 0 | 2014-01-31 | 3 | 0 |
| 0 | 2014-04-30 | 3 | 6 |
| 0 | 2014-05-31 | 0 | 0 |
| ... | ... | ... | ... |
| 0 | 2014-10-31 | 1 | 0 |
| 0 | 2014-11-30 | 1 | 1 |

*FIG. 9*

Algorithm 1: A pseudo-code for the proposed Discriminatory Sequence Mining.

Input : Collections $S_n = [S_1, S_2]$, $\sigma_{min}$, $max\_len$, $I$
Output : $S_{out}$, where $(|S_{out}| << |S_1|, |S_2|)$ such that
$\forall s \in S, ds > threshold$ 1 for : $c \rightarrow 1$ to $|S_n|$ do
2 $\quad$ $freqs_c = \Phi S_c (\sigma min)$;
3 $\quad$ $\sigma_c = \frac{1}{n} |K_{freqs_c}(I)|$;
4 end
5 for : $c \rightarrow 1$ to $|freq_n|$ do
6 $\quad$ if $S_1.isPrefix(S_2)$ *and Lift* $(freqs_c, S_1, S_2) \xi$
$\quad\quad$ $Lift(freqs_c, S_2, S_1)$ then
7 $\quad\quad$ $S_{out} = $ pruneByDominance $(freqs_c, S_1)$;
8 $\quad$ end
9 $\quad$ if $\frac{match(S_1, S_2)}{match(S_1)} > threshold$ then
10
11 $\quad\quad$ $S_{out} = $ pruneByShadows$(S_1)$;
$\quad$ end
12 end

*FIG. 10*

| Discriminatory Reason | Subsequence | Support Left | Support Right | Lift |
|---|---|---|---|---|
| (1) vs (2) | 8 → P → P | 0.26785 | 0.07596 | 3.5260 |
| (1) vs (2) | 8 → 8 → P | 0.27142 | 0.07658 | 3.5440 |
| (9) vs all other DS | 8 → 8 → 0 | 0.19821 | 0.07160 | 2.7681 |
| (1) vs all other DS | 8 → 8 | 0.30693 | 0.07666 | 4.0034 |
| (9) vs all other DS | 0 → 0 → 0 → 0 → 0<br>0 → 0 → 0<br>0 → 0 | 0.33884 | 0.10515 | 3.2222 |
| (9) vs all other DS | 0 → 0 → 0 → 0 → 0<br>0 → 0 | 0.40707 | 0.07638 | 5.3290 |

FIG. 14

| Dataset | AUC | W-AUC | τ | 95% CI |
|---|---|---|---|---|
| EHR H$_0$ | 0.77 | 0.48 | 0.064 | (0.013, 0.123) |
| EHR H$_3$ | 0.73 | 0.48 | -0.011 | (-0.036, 0.018) |

FIG. 15

| Classes | Discontinuation Classifiers | | | | | | | | | | | | |
|---|---|---|---|---|---|---|---|---|---|---|---|---|
| | Baseline | | | Extra Tree | | | LSTM | | | Bi-LSTM with Attn | | |
| | Precision | Recall | F1-Score | Precision | Recall | F1-Score | Precision | Recall | F1-Score | Precision | Recall | F1-Score |
| $R_0$ | 0.00 | 0.00 | 0.00 | 0.99 | 0.35 | 0.52 | 0.89 | 0.52 | 0.65 | 0.96 | 0.49 | 0.65 |
| $R_1$ | 0.67 | 0.99 | 0.80 | 0.75 | 0.99 | 0.86 | 0.79 | 0.97 | 0.88 | 0.79 | 0.99 | 0.88 |
| Macro Average | 0.33 | 0.50 | 0.40 | 0.87 | 0.68 | 0.69 | 0.84 | 0.74 | 0.76 | 0.88 | 0.74 | 0.76 |
| Weighted avg | 0.44 | 0.67 | 0.53 | 0.83 | 0.78 | 0.75 | 0.83 | 0.82 | 0.80 | 0.85 | 0.82 | 0.80 |

PATTERN DISCOVERY, PREDICTION AND CAUSAL EFFECT ESTIMATION IN TREATMENT DISCONTINUATION

BACKGROUND

The present invention relates to the electrical, electronic and computer arts, and more specifically, to machine learning and the like.

Continued use of medication can improve the health of a person, while improper discontinuation of medication use can be harmful. Purely by way of a non-limiting example, discontinuation from ART (anti-retroviral therapy) is known to be a significant problem across the globe. Four studies conducted in several locations reported that the proportion of long-term follow up (LTFU) was 9.8%, 26.7%, 28% and 31.4%, respectively. Discontinuation refers to stopping a particular event while the risk of the outcome for which that event was initiated still exists. In this case, the concern is stopping the use of ARTs, or not completing the steps needed to begin ART administration; i.e., 90.2%, 73.3%, 72%, and 68.6% respectively stopped proper treatment (or even failed to initiate same) while still being at risk.

Existing methods for medication treatment discontinuation typically focus on identifying high level trends using stratified analysis and descriptive statistics.

SUMMARY

Principles of the invention provide techniques for pattern discovery, prediction and causal effect estimation in treatment discontinuation. In one aspect, an exemplary method includes, with a trained, computerized discontinuation predictor machine learning component, predicting, based on an input time series, a time when a subject will discontinue a course of medical treatment; and, with a trained, computerized pattern behavior extractor machine learning component, extracting from said input time series a top k discriminatory sequences via discriminatory sub-sequence mining. Said top k discriminatory sequences differentiate between first and second classes of interest to provide a hypothesis for downstream analysis of a cause of discontinuing said course of medical treatment. Further steps include, with a trained, causal effect estimator computerized machine learning component, determining a reason why said subject will discontinue said course of medical treatment, based on said top k discriminatory sequences and additional data; and, with a computerized user interface, providing said time when said subject will discontinue said course of medical treatment and said reason why said subject will discontinue said course of medical treatment to a responsible party to initiate an intervention.

In another aspect, an exemplary system includes a memory; a non-transitory computer readable medium comprising computer executable instructions; and at least one processor, coupled to said memory and said non-transitory computer readable medium, and operative to execute said instructions to instantiate a trained, computerized discontinuation predictor machine learning component, a trained, computerized pattern behavior extractor machine learning component, a trained, causal effect estimator computerized machine learning component, and a computerized user interface. The at least one processor is further operative to, with said trained, computerized discontinuation predictor machine learning component, predict, based on an input time series, a time when a subject will discontinue a course of medical treatment; and, with said trained, computerized pattern behavior extractor machine learning component, extract from said input time series a top k discriminatory sequences via discriminatory sub-sequence mining. Said top k discriminatory sequences differentiate between first and second classes of interest to provide a hypothesis for downstream analysis of a cause of discontinuing said course of medical treatment. The at least one processor is further operative to, with said trained, causal effect estimator computerized machine learning component, determine a reason why said subject will discontinue said course of medical treatment, based on said top k discriminatory sequences and additional data; and, with said computerized user interface, provide said time when said subject will discontinue said course of medical treatment and said reason why said subject will discontinue said course of medical treatment to a responsible party to initiate an intervention.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

These and other features and advantages of the present invention will become apparent from the following detailed description of illustrative embodiments thereof, which is to be read in connection with the accompanying drawings.

BRIEF DESCRIPTION OF THE DRAWINGS

FIG. 3 is a table of discriminatory subsequences mined in the subpopulation of patients that discontinue due to health concerns, as opposed to the rest of the population that discontinue for any other reason, useful in connection with aspects of the invention;

FIG. 9 shows an example of calendar data for an exemplary individual, useful in connection with aspects of the invention;

FIG. 10 shows exemplary pseudo-code for discriminatory sequence mining, according to an aspect of the invention;

FIG. 14 shows examples of discriminatory subsequences with particular discontinuation reasons obtained produced using aspects of the invention;

FIG. 15 shows evaluation of a calibrated logistic regression propensity model trained on the datasets with common support between the treatment groups, the average treatment effect, and the 95% confidence interval produced using aspects of the invention;

DETAILED DESCRIPTION

Figure 1:
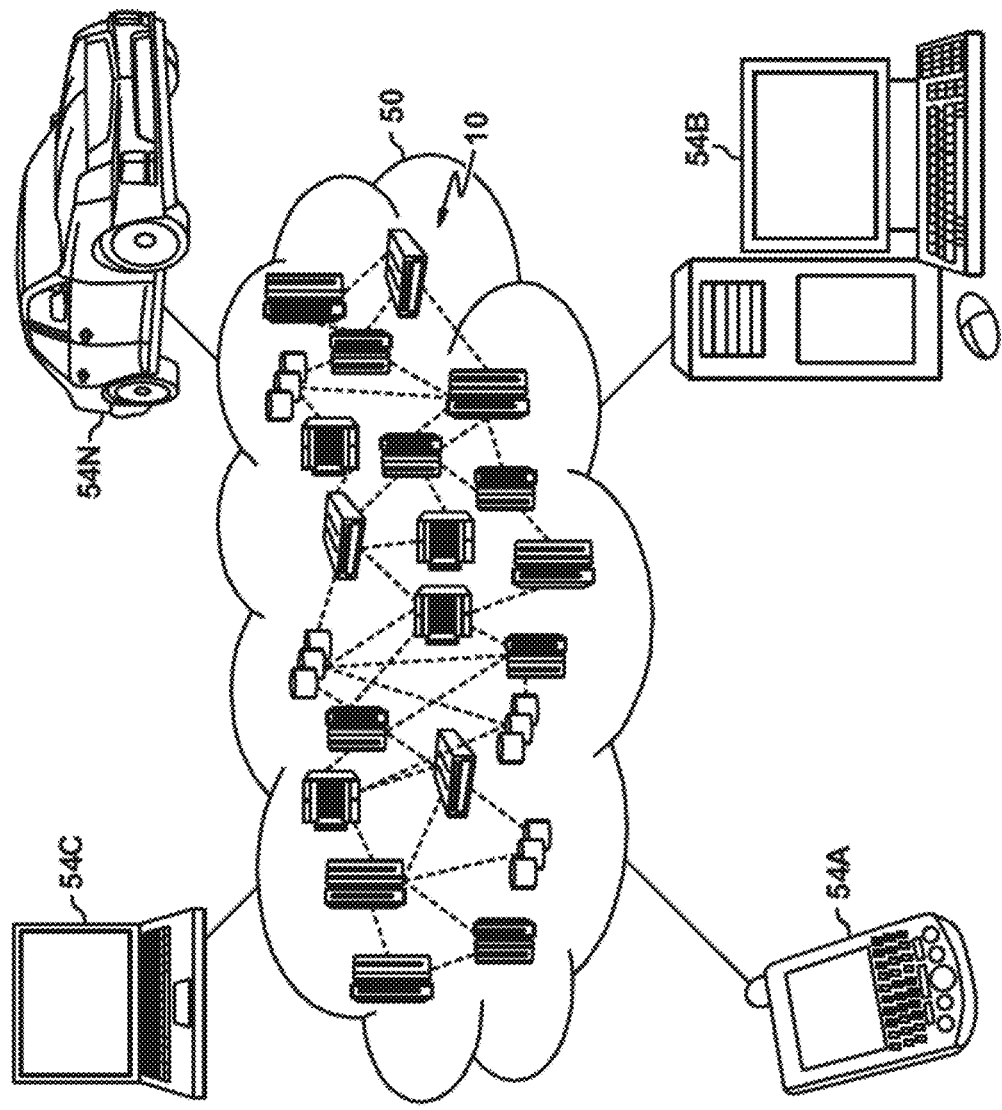
FIG. 1 depicts a cloud computing environment according to an embodiment of the present invention.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations).

It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
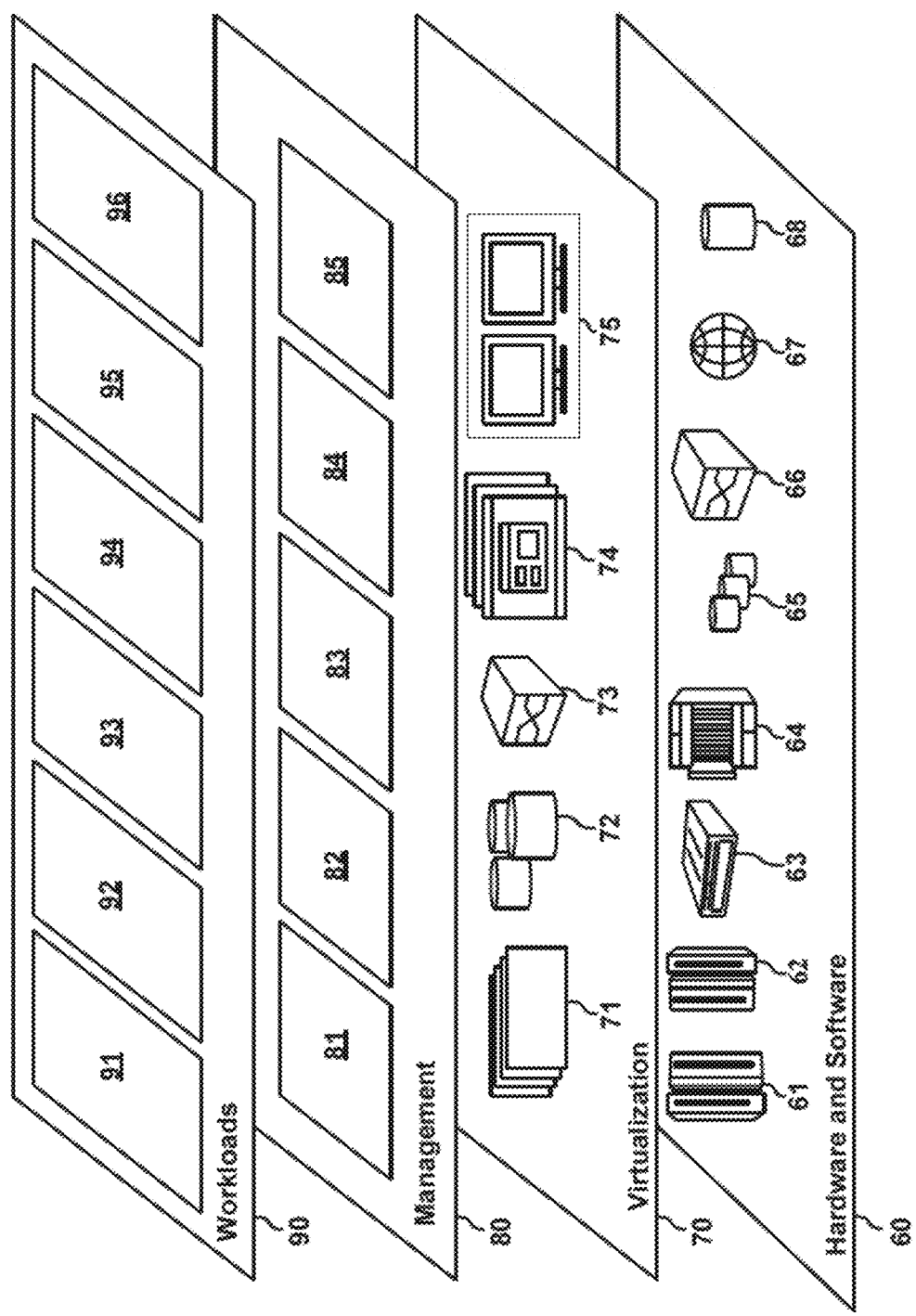
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a cloud-based service 96 (or one or more elements thereof) to provide pattern discovery, prediction and causal effect estimation in treatment discontinuation.

Aspects of the invention provide pattern discovery, prediction and causal effect estimation in medical treatment discontinuation. Advantageously, unlike prior art techniques, one or more embodiments address temporal associations, that is, associations regarding more than one time-step (e.g., via discriminatory sequence mining); non-linear associations for predicting discontinuation (e.g., via recurrent neural networks); and/or causal mechanisms present in reasons for discontinuation (e.g. via inverse probability weighting). Indeed, one or more embodiments provide techniques for automated discovery of patterns, prediction and causal effect estimation in treatment discontinuation. One or more embodiments provide automatic generation of a behavior hypothesis of medication uptake and/or causal mechanisms that verify the hypothesis (generated in the prior step) with inverse probability weighting. The disclosed techniques can be applied to a wide range of domains such as chronic disease contexts and comorbidities (e.g., diabetes, hypertension, or other heart and/or metabolic conditions).

Indeed, one or more embodiments predict, detect, and characterize behaviors on treatment discontinuation based on the analysis of calendar event data, including: identifying dynamics and determinants of medication treatment use and discontinuation; identifying discriminatory temporal/sequential patterns in the type of medication treatment use and reasons for discontinuation using calendar event data and sub-sequence mining methods; and estimating the effect of specific variables on discontinuation outcomes based on the temporal/sequential patterns. Disclosed also are techniques for providing end user (subject-matter experts) insights on discriminating patterns and their causal effect on discontinuation for further investigation and to support decision-making. One or more embodiments thus provide techniques to automatically generate a hypothesis for analyzing medication uptake behavior from calendar events using the Discriminatory Sub-sequence Mining method; and/or techniques to perform causal analysis and testing of all hypotheses based on the output of the discriminatory sub-sequence mining.

Figure 8:
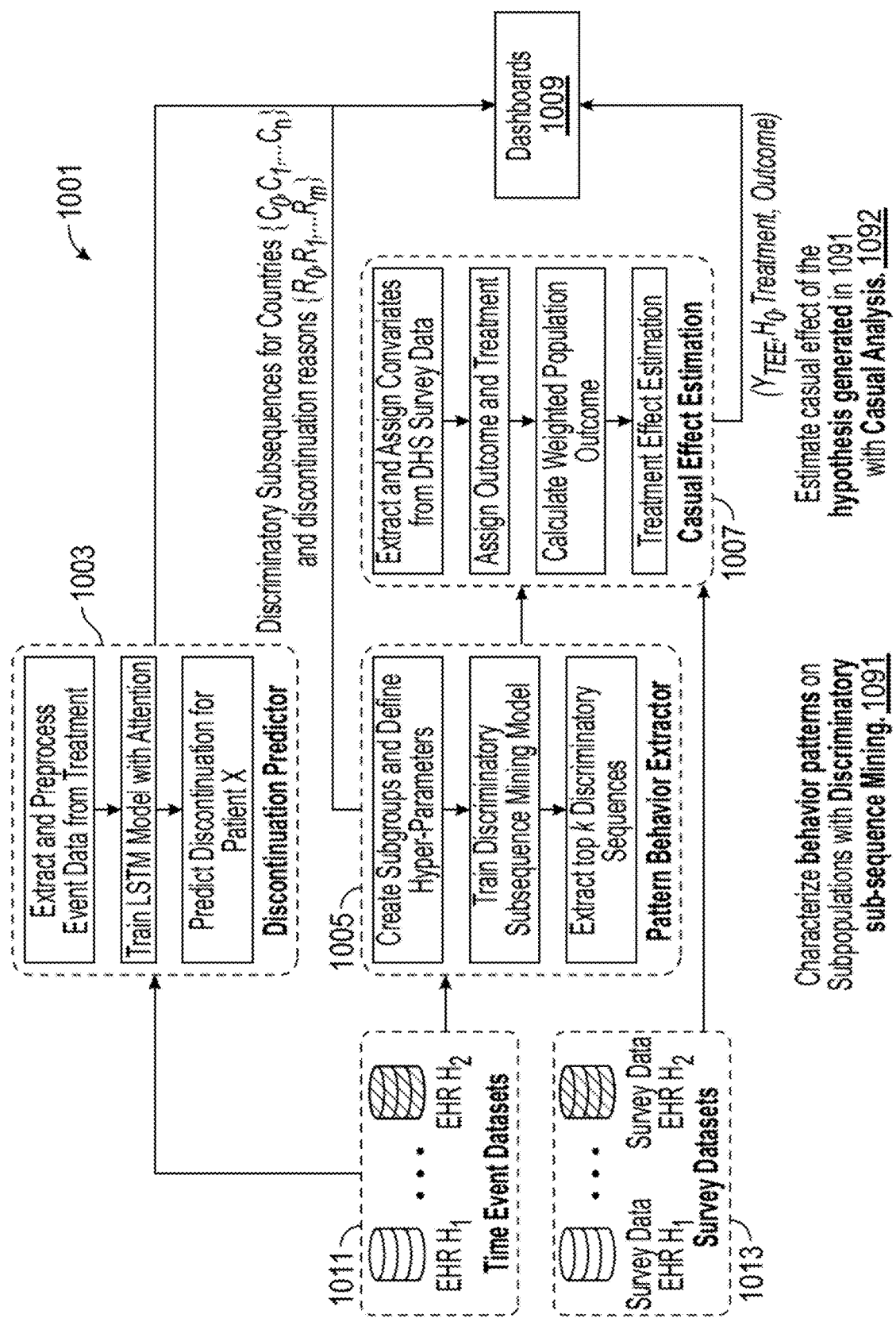
FIG. 8 shows an exemplary system, according to an aspect of the invention.

FIG. 8 illustrates an exemplary system 1001 and method(s) for pattern recognition, prediction, and causal effect estimation for medication discontinuation, according to aspects of the invention. Hypothesis generator 1005 is also referred to herein as a pattern behavior extractor. In one step, as seen at 1091, characterize behavior patterns on subpopulations with discriminatory sub-sequence mining. In another step, as seen at 1092, estimate the causal effect of the hypothesis generated at 1091 with causal analysis. In one or more embodiments, predictor 1003 applies Long-Short-Term Memory Networks (LSTM) models. The LSTM processes input sequences of treatment episodes, e.g., n consecutive months, by recursively applying a transition function to its internal hidden state vector $h_t$, where $t \in 1 \ldots n$. The activation of the hidden state $h_t$ at time step t is computed as a function f of the current treatment episode $e_t$ and the previous hidden state $h_{t-1}$. The final hidden layer $h_T$ is the representation of the complete sequence of episodes during the last t months prior to the discontinuation. This layer has a fully connected layer followed by a SoftMax non-linear layer that predicts the probability of discontinuation for a particular reason, for the input sequence of episodes.

In one or more embodiments, extractor 1005 uses software to implement the logic described in the section herein entitled "Data-driven Discriminatory Sequence Mining." Furthermore, in one or more embodiments, estimator 1007 uses software to implement the logic described in the section herein entitled "Causal Effect Estimation for Discontinuation Reasons."

Thus, shown in FIG. 8 is an exemplary computing system 1001 that includes a medical treatment discontinuation predictor 1003, a pattern behavior extractor 1005 (which extracts patterns related to the treatment usage), and a causal effect estimator 1007 (which estimates effects, due to discontinuation of the treatment(s), of a person undergoing one or more medical treatments). Also included are a set of visualization dashboards 1009 configured with communication devices (e.g., phone, personal computer, etc.—not shown) for assisting a domain expert or a group of domain experts in understanding, characterizing, and interpreting reasons why the person discontinued the one or more medical treatments (e.g., chronic disease treatments such as for diabetes or heart conditions). FIGS. 6, 11, 12, and 13 are non-limiting examples of graphics that can appear on dashboards 1009. The visualization dashboards also provide subject-matter experts insights on discriminating patterns and their causal effect on discontinuation for further investigation and to support decision-making.

Figure 19:
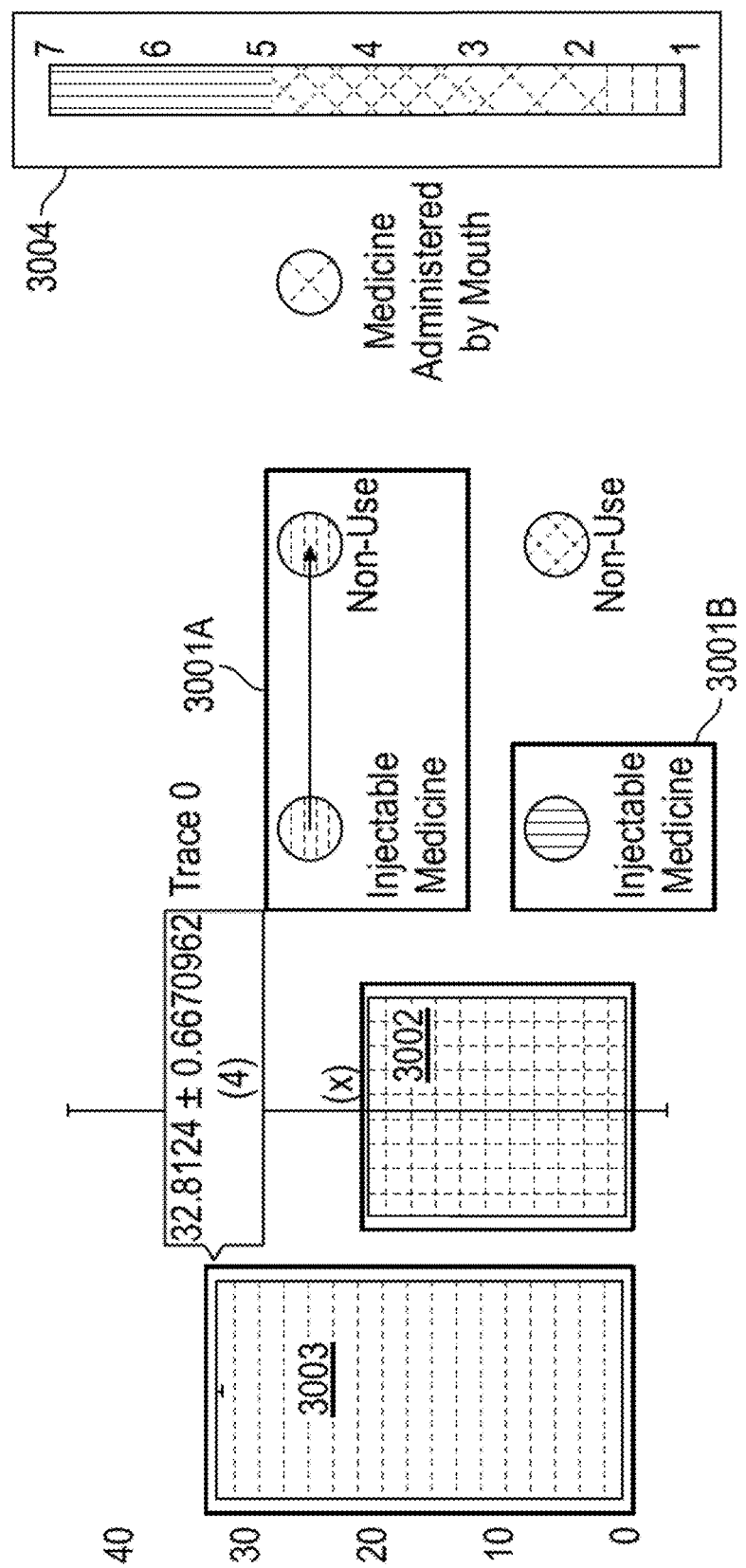
FIG. 19 shows a user interface, in accordance with aspects of the invention, including discriminatory sub-sequences regarding a reason for a dataset.

In one or more embodiments, the computing system processes personal historical datasets, including data related to treatments, such as time event data 1011 and survey data 1013. Of course, all health data and the like should be gathered and used in accordance with all applicable privacy laws and regulations, with appropriate use of anonymization and the like. The computing system includes a number of components as described in greater detail elsewhere herein. In one or more embodiments, the visuals used to represent the discriminatory sub-sequences use a combination of a bar plot to show coverage and a shaded scatter plot to show the sequences. Refer to FIG. 19, for example. Shown in FIG. 19 are discriminatory sub-sequences regarding reason $R_1$ for a data set of electronic health records (HER) $H_4$. Elements 3001A and 3001B depict sub-sequences. Each event, e.g., injectable medicine is repeated n number of times where n is indicated using the corresponding grayscale intensity on the scale bar 3004 (color scale could also be used if desired). A sub-sequence may include a single repeated event as in 3001B or multiple events linked with an arrow as in 3001A. At 3002, support right refers to the support value of the pattern for the right dataset (X) aggregated for all individual sub-sequences; i.e., compute the mean and standard deviation. At 3003, support left refers to the support value of the pattern for the left dataset aggregated for all individual sub-sequences; i.e., compute the mean and standard deviation (in the non-limiting example mean 32.81 plus or minus one standard deviation 0.667). Scale bar 3004 shows the number of times an event is repeated in a sub-sequence.

With attention again to FIG. 8, in one or more embodiments, the medical treatment discontinuation predictor 1003 preprocesses treatment datasets to construct a data set X for training a machine learning model. The machine learning model is based, for example, on LSTM that encodes each sample in X to a set of vectors (vector space) for training and testing the LSTM model. In one or more embodiments, let a time series sequence $s_i = (e_{c,t-(n-1)}, \ldots, e_{c,0})$, be the sequence of episodes, $e_{c,t}$, represented by the type of medicine used, c, and the month during which the medication was used, t=mm/yyyy, by subject i (e.g., an individual captured by an event-based calendar including data related to demographics and/or health which includes, e.g., time stamp data on when a medicine was taken by the patient or an activity of the treatment performed (such as a doctor's appointment)). Then, let n be a pre-specified integer representing the number of months (time steps) prior to the event $Y_i \in \{reason_1, reason_4\}$ that occurred at t, for subject i. Next, $X_i = \{s_{i1} \ldots s_{im}\}$, is the set with all m sequences found for subject i, with an event $Y_i$. Finally, construct data set $X = \{X_1 \cup \ldots \cup X_j\}$ for all j subjects.

In one or more embodiments, the pattern behavior extractor 1005 uses sub-sequence mining techniques to compute common medication pattern behaviors over medication calendar data for specific subpopulations. The extractor 1005 takes two cohorts to discriminate. First, given two classes ($group_A$ and $group_B$) of the problem, it searches for differentiating sequences among them. There are two parameters that need to be set, $\sigma_{min}$ and max_len. The first expresses a threshold on how often a particular pattern occurs (in terms of the minimum percentage across all the sequences in calendar data). The patterns identified are sequential in nature and are sub-sequences (a sub-sequence corresponds to an element in the set of all event sequences) of the medication uptake patterns. In one or more embodiments, the method of extracting pattern behavior further includes performing pattern mining on calendar data to check for common patterns in those patients that discontinue their medication uptake. These patterns serve as a hypothesis for downstream causal analysis to determine if, and to what extent, there exists a causal relationship to discontinuation.

Consider hypothesis generation. In one implementation example, the sequential calendar data is analyzed using an inventively modified version of known sequence mining techniques. Refer, for example, to Jian Pei, Jiawei Han, B. Mortazavi-Asl, Jianyong Wang, H. Pinto, Qiming Chen, U. Dayal, and Mei-Chun Hsu, Mining sequential patterns by pattern-growth: the prefixspan approach, IEEE Transactions on Knowledge and Data Engineering, 16(11):1424-1440, November 2004. One non-limiting example of a suitable library that extends the known PrefixSpan technique is IBM Cloud SQL Query, available from International Business Machines Corporation, Armonk, N.Y., USA, which supports a wide variety of time series functions as native components of the service (referred to hereinafter as the IBM Time Series Library). In one or more embodiments, these known techniques are enhanced for analysis of medication treatment datasets, since the large amount of data and the unique journey of a person in treatment (e.g., patients under different heart disease treatments) need to be analyzed and encoded differently than the original out-of-the-box techniques implemented in IBM Time Series Library. In particular, this method mines very large numbers of frequent sequences that are often not unique to the subgroup of interest and hence largely unusable for manual inspection by an analyst.

Thus, one or more embodiments extend the PrefixSpan algorithm to analyze large-scale and noisy data. One or more embodiments then compare two subgroups and mine patterns that would only appear predominantly in one of the subgroups. These extensions are referred to herein as the Discriminatory Sub-sequence Mining (DSM) technique. In one or more embodiments, after a DSM model is trained, n discriminatory sub-sequences are extracted for each database EHR $H_j$, and the top k more discriminatory sequences are retained, based on lift metrics. In another aspect, one or more discontinuation hypotheses ($H_i$) and pieces of treatment information ($t_i$) are generated and are used to estimate the effect of factors on medication discontinuation.

Further regarding discontinuation predictor 1003, one or more embodiments train a custom machine learning algorithm (e.g., LSTM) to predict when a person is going to discontinue a particular medication. The Discontinuation Predictor takes input from time event datasets 1011, defined as $X_i$ and $Y_i$ (historical information) for training and validating the machine learning model. Standard preprocessing can be carried out in one or more embodiments; e.g., removing outlier samples, standard scaling or normalization, data imputation when missing values are found, and the like. In one or more embodiments, the output of the LSTM is disc reason (reason why a patient discontinues a particular treatment, when a patient will discontinue, and the probability for such discontinuation).

In another aspect, one or more embodiments can be used for predicting non-adherence for diseases that can progress or regress to different stages. Here, HIV is a useful example as it has four stages of progress that are monitored by data captures in both clinical and non-clinical-care settings (HIV is, however, but one non-limiting example of a viral disease to which aspects of the invention could be addressed). One or more examples focus on non-clinical care settings where patients are visited by an "at home nurse" or "community health worker" (CHW) on a monthly basis to provide patient surveillance and additional information to support medication adherence. For example, patients may progress or digress into different stages of their condition (in HIV there are four stages that are monitored throughout a patient's lifetime through multiple points of data collected at regular intervals). In this case, discontinuation will ultimately lead to increase in viral load and risk to the community. Specific observations of the patient can be considered to be time-varying, particularly those activities that lead to non-adherence or loss-to-follow-up (more than 128 days not visiting a clinic).

Other examples of data collected in in-home settings are indications of alcohol use or other contraindicative uses (e.g. smoking etc.), needle use, high risk behavior, types of food consumed, collecting physiological and psycho-social data of the patient in the home setting. These can be categorized and logged, creating a set of time-based events that can be used for sequences and prediction of unwanted events: experiencing side effects, non-adherence, dropping out, etc.

In general, one or more embodiments can analyze any time-based series of events that leads up to an at-risk event, such as non-adherence, loss-to-follow-up (unable to retain patient), and the like. Another way to look at "discontinuation reasons" is to equate them to known side effects.

In one or more embodiments, the causal effect estimator 1007 uses both information from the sub-sequences found by the pattern behavior extractor 1005 and EHR (Electronic Health Record (EHR) here is used in a general sense to mean health and or demographic data which may include, for example, indicators of health, wealth, lifestyle preferences, family structure, education, and the like) from survey datasets 1013. $H_0$, treatment (A) and outcome (Y or $R_i$) are extracted from the discriminatory sub-sequence and L (see definition below) from the EHR database. A series of steps are conducted from the observational data obtained from each individual record of the EHR data.

It is desired to evaluate whether use of a particular medication/treatment method (extracted from the hypothesis generator 1005) had a causal effect on discontinuation for health concern reasons. Define a sequence of steps. The null hypothesis $H_0$ is that the average of the individual causal effects is 0. Define L to be the set of covariates for each individual in the EHR database. The outcome Y is defined as whether or not a patient surveyed in the EHR reported discontinuation for reason $R_i$ (the discontinuation reason is extracted from the two subgroups in the hypothesis generator 1005). Then, create the treatment assignment A based on the use of that medication/treatment in the past year. Based on whether or not the longest consecutive method in the past 12 months was the method found in hypothesis generator 1005, assign that individual to treated or untreated groups. With that problem setup, use Inverse Probability Weighting (IPW) with stabilized weights to calculate weighted population outcome for each subgroup, stratified by treatment assignment. Calculate the treatment effect by subtracting the outcome of the untreated group from the treated group.

In one or more embodiments, from the causal analysis, if causal reasons are found, they can be used to target personalized data collection during an at home visit to a patient by an "at home" nurse or "community health worker." Then, survey questions that are used during the visit can be tailored to understand what is happening, and to provide insight for defining the right type of personalized intervention, i.e. adaptive community health worker surveys for patient surveillance in the home.

Figure 4:
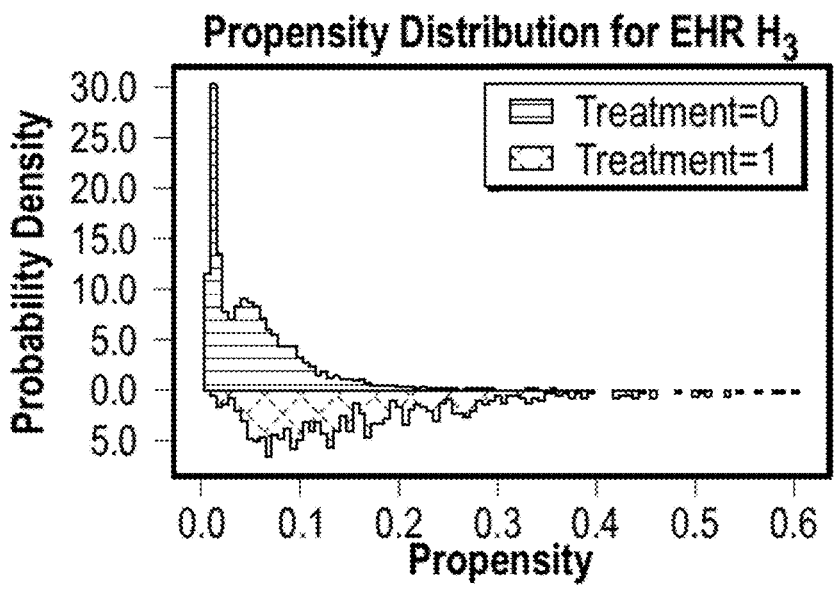
FIGS. 4 and 5 show propensity distributions for two different treatments for two different jurisdictions, useful in connection with aspects of the invention.
Figure 5:
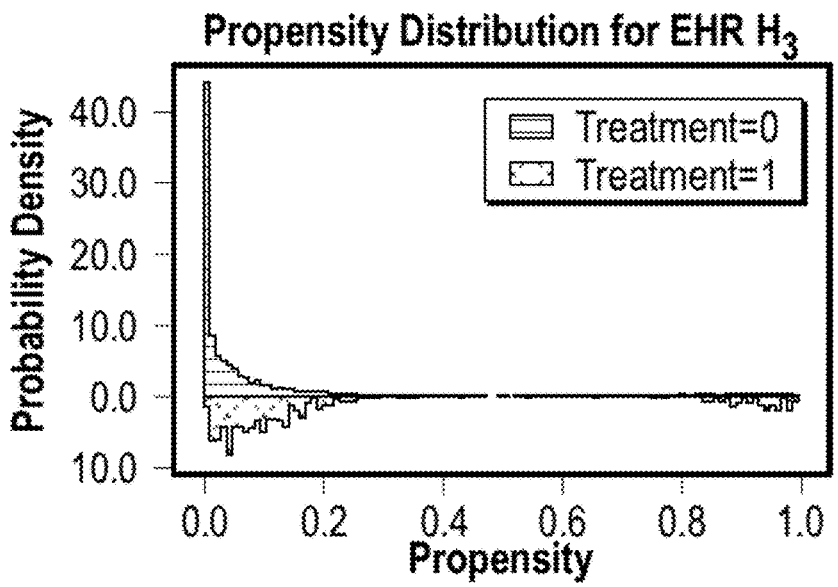
Figure 6:
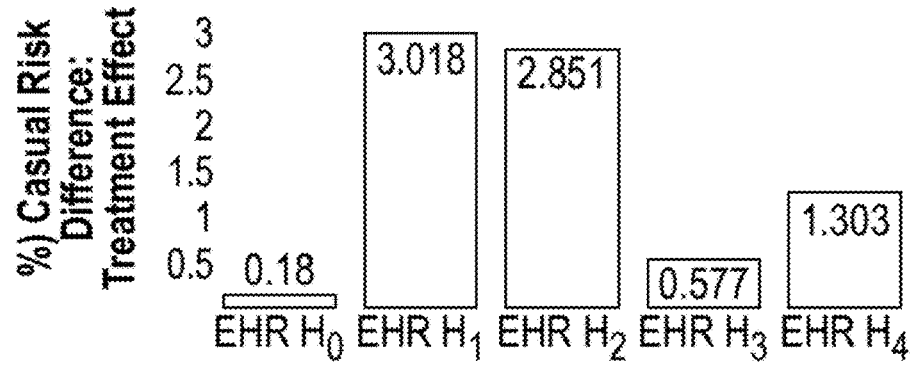
FIG. 6 shows causal effect estimation of treatment on discontinuation for health concerns for five different jurisdictions, useful in connection with aspects of the invention.
Figure 7:
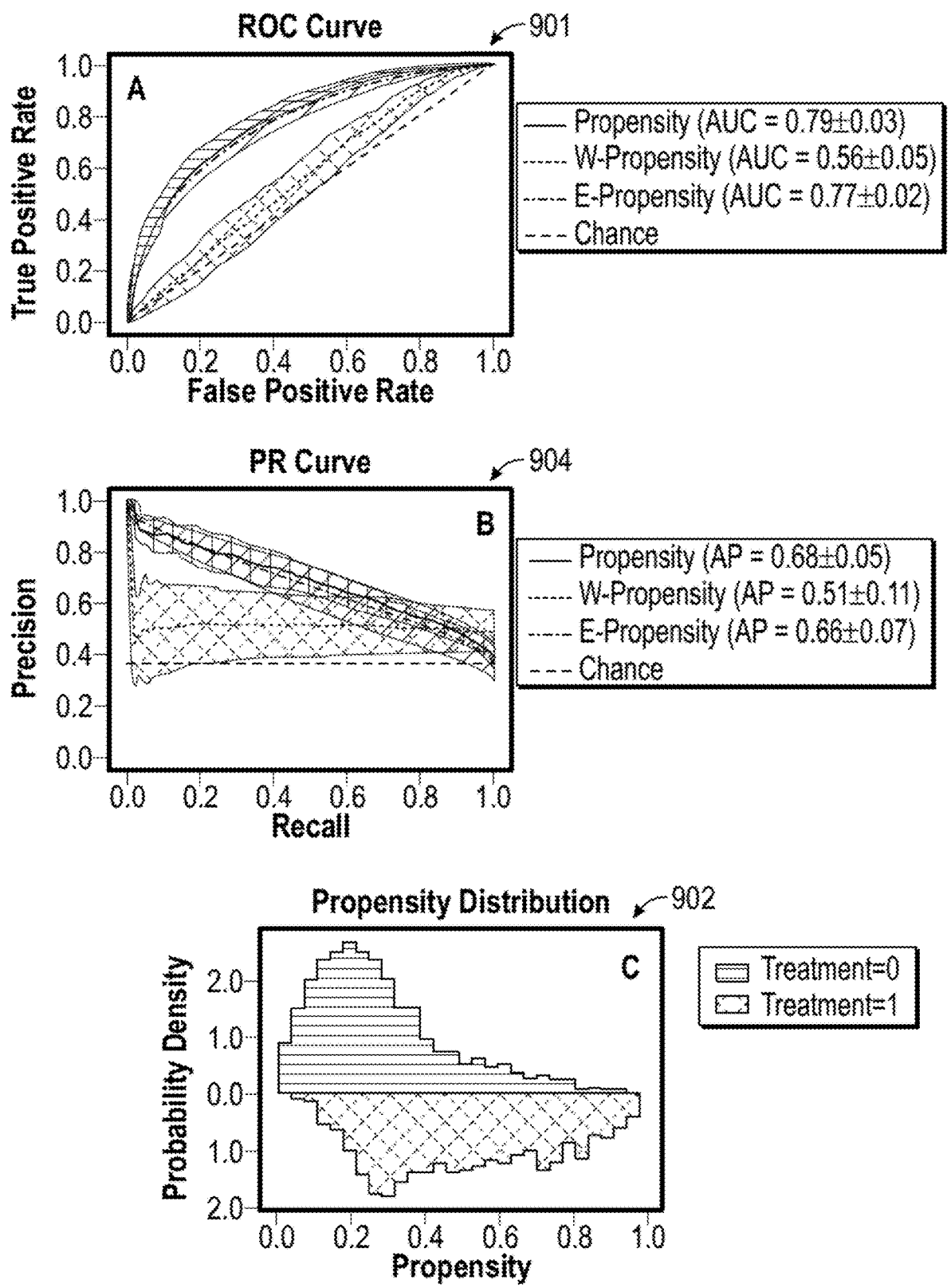
FIG. 7 shows performance of a base estimator, propensity distribution, how predicted probabilities vary from the distribution of observed probabilities, and the distribution of the standard mean difference of values for each covariate between two groups, useful in connection with aspects of the invention.
Figure 7:
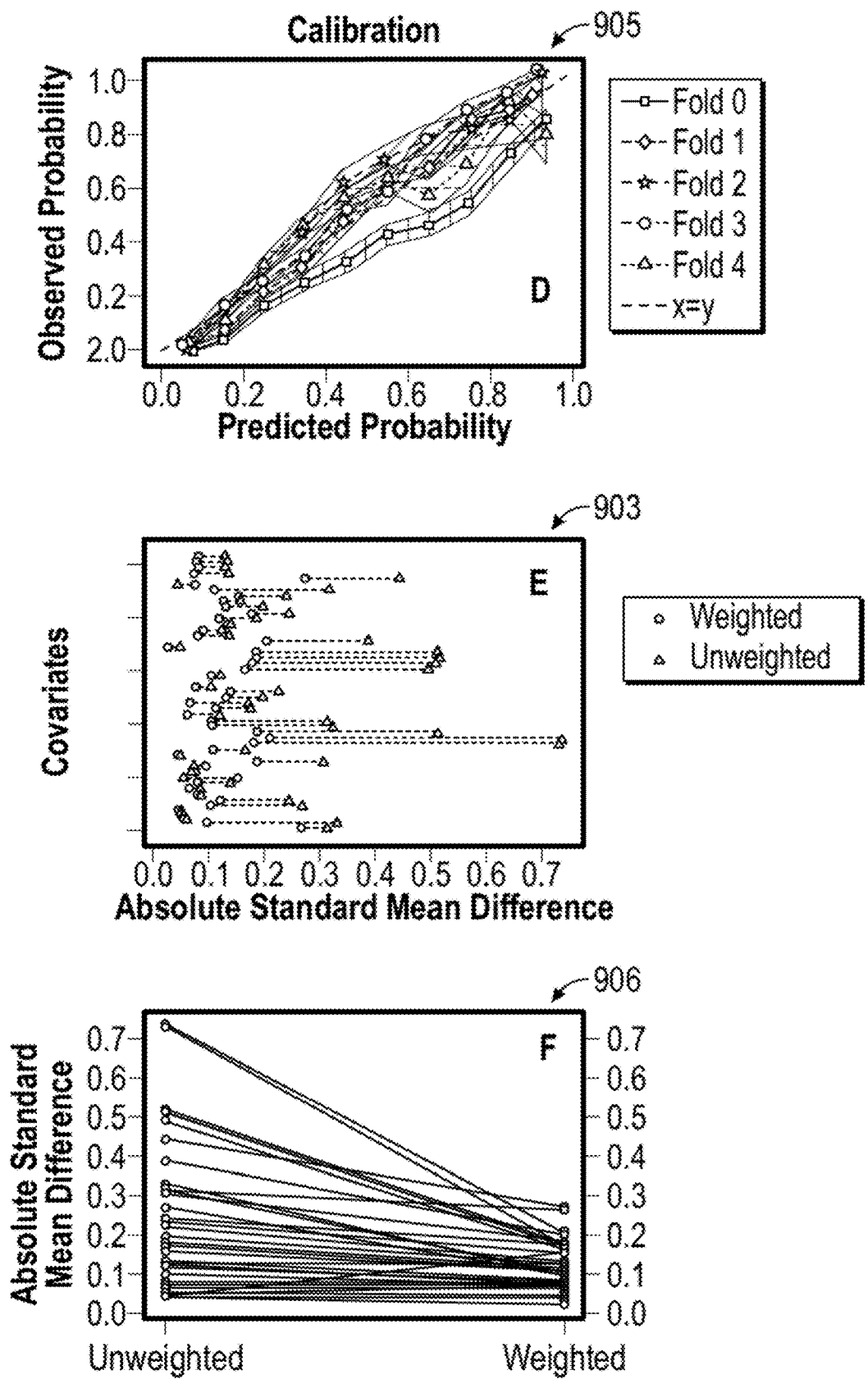

FIGS. 4, 5, 6, and 7 show examples of visualizations from the Causal Effect Estimator 1007 for a given generated hypothesis Ho. The visualizations advantageously assist in evaluating the performance and reliability of the outputs from the causal effect estimator. FIGS. 4 and 5 show propensity distributions for two different treatments, 0 and 1, for two different jurisdictions, EHR $H_3$ and EHR $H_4$. FIG. 6 shows causal effect estimation of treatment on discontinuation for health concerns for five different jurisdictions; namely, EHR $H_0$, EHR $H_1$, EHR $H_2$, EHR $H_3$, and EHR $H_4$. In FIG. 7, curves 901, 904 are ROC Curves and PR Curves (standard performance indicators) showing the same thing in different ways. i.e., the performance of the IPW base estimator before and after the IP-Weights. Curve 902 presents the propensity distribution showing the marginal distribution of the two groups and where they do or do not overlap. Curve 905 shows how the predicted probabilities vary from the distribution of observed probabilities in the data for five folds/splits of the dataset. Curves 903, 906 show the distribution of the standard mean difference of values for each covariate between the two groups.

Figure 12:
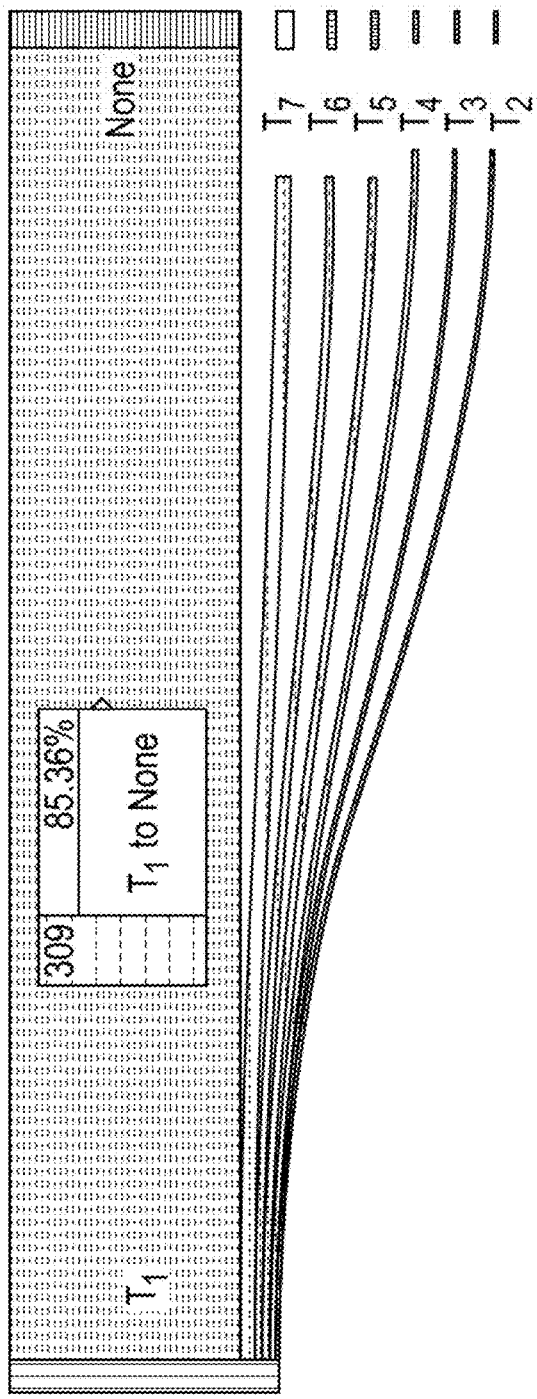
FIGS. 12 and 13 show exemplary Sankey plots produced using aspects of the invention.
Figure 13:
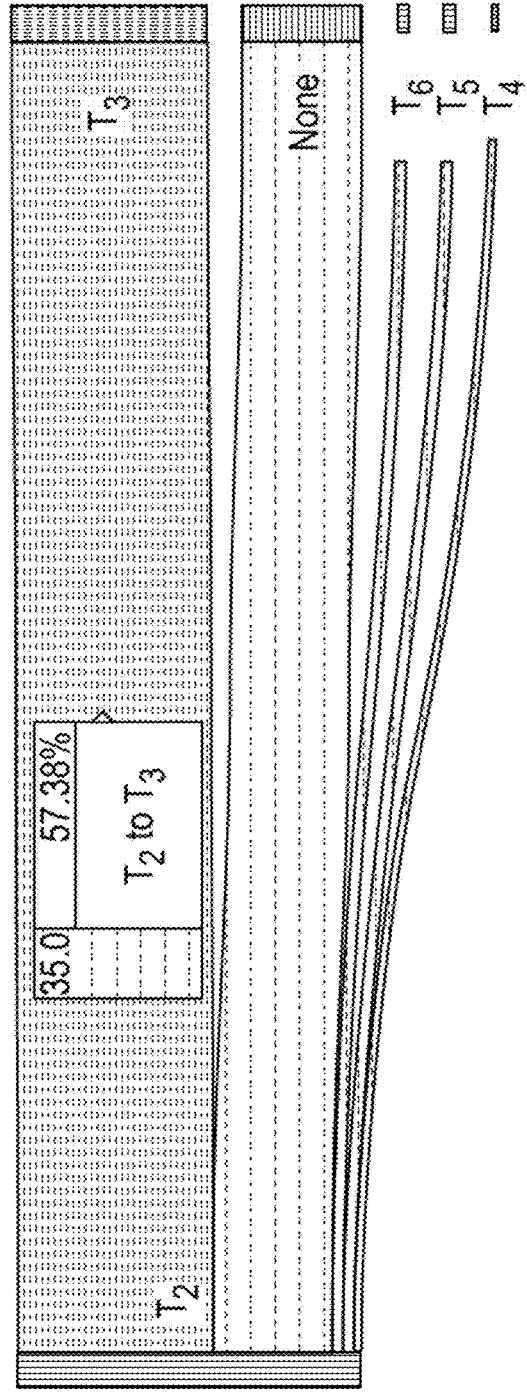

One or more embodiments generate one or more decision dashboards 1009 to provide end users (subject-matter experts) with insights on discriminating patterns and their causal effect on discontinuation, for further investigation and to support decision-making. In one or more embodiments, the decision dashboard is implemented using interactive violin plots to display consecutive months per treatment/medication type and subgroup (multiple selections for comparisons are available). Furthermore, to easily interact with treatment switching patterns, one or more embodiments employ Sankey plots, where the source and target can be set by the domain expert. FIGS. 12 and 13 show exemplary interactive Sankey plots for transitions from two different types of episode. For sequence mining insights, one or more embodiments use a combination of directed graphs and bar plots (for support metrics). For causal analysis, one or more embodiments display average treatment effect and several evaluation metrics of the estimator, such as violation of positivity, consistency, balanced covariates, and accuracy of the propensity model.

One exemplary goal with sequence mining is to identify medication uptake patterns that may be unique to one cohort of persons (e.g., people that discontinued due to health concerns). Extracting such patterns not only sheds light that is invaluable to domain experts, but can also have predictive power—for example, being able to predict that a discontinuation event may occur in k steps if a particular pattern is being observed.

One or more embodiments extend the PrefixSpan algorithm to mine for patterns that are different between two classes of interest. In one or more embodiments, there are two parameters that are set, σ_min and max_len. Each pattern that is found is reported and tagged is tagged with various metrics. Support left and right is the support $$\sigma_T = \frac{1}{n} |K_T(I)|$$

of a pattern T, for left and right datasets. Lift(T, left, right), is the ratio of $$\frac{\sigma_T^{left}}{\sigma_T^{right}}$$

defining how much more often a pattern occurs in the left dataset as compared to the right. When this number is very large, it indicates that the pattern is unique to the left dataset. The discriminative patterns that are found serve, for example, as hypothesis(es) for downstream causal analysis to determine if and to what extent there exists a causal relationship to discontinuation.

An example pseudo-code algorithm for DSM is shown in FIG. 10. The inputs include $S_1$ and $S_2$, which are two collections of sequences (e.g., those that continue medication use vs. those that do not); the time window to be analyzed (max_len); the minimal support required ($\sigma_{min}$); and the item set I. The output $S_{out}$ includes one or more patterns with discriminatory power greater than a threshold. In the FOR-END construct of lines 1-4 of the pseudocode of FIG. 10, for each collection of sequences, determine the support left and right. In the FOR-END construct of lines 5-12 of the pseudocode of FIG. 10, for each identified pattern, carry out pruneByDominance (discussed further below) in the IF-THEN construct at lines 6-8, and carry out pruneByShadows in the IF-THEN construct at lines 9-11 (see discussion of matching elsewhere herein).

The table of FIG. 3 illustrates, as an example, all subsequences found under health concern discontinuations contained episodes of an injectable medicament as a treatment method according to an exemplary embodiment. Additionally, it can be observed that the patterns for several datasets are discriminant (See Support Left, Support Right and Lift values) while the last pattern containing Injectables was not discriminant for the health concern discontinuations. The table of FIG. 3 thus illustrates discriminatory sub-sequence examples found across all datasets searching in groups with discontinuations reasons due to health concerns opposed to the rest of the population with other discontinuation. Stated differently, the table of FIG. 3 shows discriminatory subsequence examples for the subpopulation with discontinuation reasons due to health concerns when compared with the subpopulation that discontinued for other reasons. Code: "3" refers to treatment $T_3$ and "0" to non-use.

In one or more embodiments, in the task of discontinuation prediction, a useful strategy is to map the input sequence of episodes to a fixed-sized vector representation using a Recurrent Neural Network (RNN), and then feed the vector to a softmax layer for classification on the type of discontinuation. Given a series of episodes $e=\{e_0, e_1, e_2, \ldots, e_T\}$, first use a lookup layer to obtain the representation vector/embedding for each episode $e_i$ for examples of episodes types). The output at the last moment $h_T$ can be regarded as the representation of the whole sequence of episodes during the last six months prior to the discontinuation, which has a fully connected layer followed by a softmax non-linear layer that predicts the probability of a particular reason of discontinuation for that time window of episodes.

$$L(\hat{y}, y) = -\sum_{i=1}^{N} \sum_{j=1}^{C} y_i^j \log(\hat{y}_i^j),$$

where $y_i^j$ is the ground-truth discontinuation reason, and $\hat{y}_i$ are the prediction probabilities. N denotes the number of training samples and C is the discontinuation reason type.

Figures 17, 18:
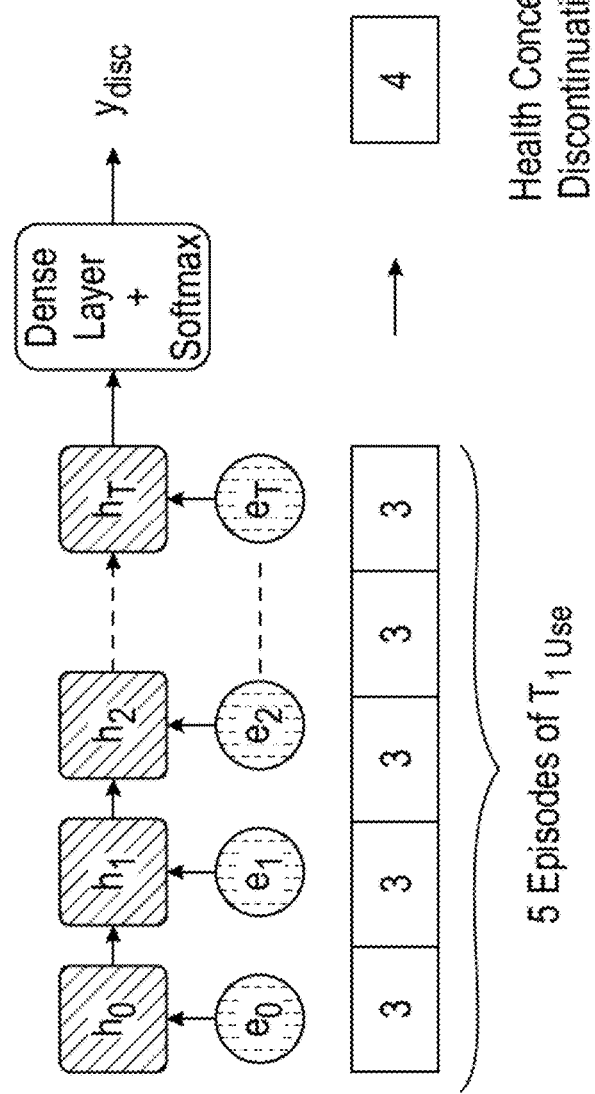
FIG. 17 shows a Recurrent Neural Network (RNN) for discontinuation prediction, according to an aspect of the invention.
FIG. 18 shows performance metrics for several classifiers, including metrics for two types of discontinuation reasons, useful in connection with aspects of the invention.

FIG. 17 shows a Recurrent Neural Network (RNN) for discontinuation prediction. Consider an example of a time window of five months using injectable medicaments (code 3) as a treatment method and in the 6$^{th}$ month discontinue due to health concerns (code 4). The RNN processes input sequences of treatment episodes, $e_0, e_1, e_2, \ldots, e_T$, to obtain the hidden state vector $h_T$, $h_0, h_1, h_2, h_T$. The hidden state $h_t$ at time step t is computed as a function of the current treatment episode $e_t$ and the previous hidden state $h_{t-1}$. The final hidden layer $h_T$ is the representation of the complete sequence of episodes during the last t time periods prior to the discontinuation. This layer is followed by a dense layer and a SoftMax non-linear layer that predicts the probability of discontinuation $Y_{disc}$ for a particular reason, for the input sequence of episodes.

The table of FIG. 18 shows performance metrics for several classifiers, including metrics for two types of discontinuation reasons ($R_0$ and $R_1$).

In another aspect, one or more embodiments estimate the effect of an intervention on some outcome from observational data. In one example, train a predictor of discontinuation (outcome in the causal analysis) using socio-economic and demographic covariates (observational data). This way, the effect of increasing the literacy level on the outcome can be estimated. To achieve this, key variables can be conditioned, identifying groups of people with the same covariates where individuals in one group are "treated" or receive an intervention, e.g. a higher literacy level, and the other group do not. Pairs of treated and untreated individuals who are very similar to each other thus provide the counterfactual estimate for each other. The average treatment effect (ATE) can then be calculated on those who were "treated" by averaging the difference in outcomes between the treated and untreated individuals.

For each causal analysis, conduct a series of steps from the observational data obtained from each individual record of the EHR data. It is desired to evaluate whether use of a medication had a causal effect on discontinuation for health concern reasons. The null hypothesis $H_0$ is that the average of the individual causal effects is 0. Define L to be the set of covariates for each individual in the dataset. The outcome Y is defined as whether or not an individual reported "discontinuation for health concern reason" (code 4) i.e. side effects in the past year (12 months) from the survey. Create the treatment assignment A based on the use of injectable medicaments in the past year. Based on whether the longest consecutive method in the past 12 months was injectable medicaments or not, assign that individual to treated or untreated groups. With that problem setup, use Inverse Probability Weighting (IPW) with stabilized weights to calculate weighted population outcome for each subgroup stratified by treatment assignment. Given the teachings herein, the skilled artisan will be able to adapt known techniques of Inverse Probability Weighting (IPW) to implement one or more embodiments (refer, e.g., to the Wikipedia article on the Horvitz-Thompson estimator and to Paul R. Rosenbaum and Donald B. Rubin, The central role of the propensity score in observational studies for causal effects, Biometrika, 70(1):41-55, 1983). Calculate the treatment effect by subtracting the outcome of the untreated group from the treated group.

If desired, evaluation plots can be generated for estimating the causal effect of education level on discontinuation using IPW with a gradient boosting classifier learner. educational interventions can be targeted towards groups that have been disadvantaged from an educational standpoint.

One or more embodiments thus provide techniques to predict, detect, and characterize behaviors on treatment discontinuation, including identifying one or more dynamics and determinants of medication treatment use and discontinuation of a given user; identifying discriminatory temporal/sequential patterns in the type of medication treatment use and reasons for discontinuation using the user's calendar event data, and; (for the hypothesis generated in the preceding step) estimating the effect of specific variables on discontinuation outcomes based on the temporal/sequential patterns.

Some cases include training a machine learning algorithm for sub-sequence mining discovery using calendar event data to find discriminatory temporal patterns in the type of medication treatment and reasons for discontinuation.

Some embodiments include automatically generating a hypothesis from the sequences for causal effect estimation due to medication discontinuation.

In some instances, performing causal analysis based on the generated hypothesis to estimate the effect of specific variables on discontinuation outcomes.

In some cases, estimating the effect of an intervention on an outcome from observational data is carried out by training a machine learning model that predicts discontinuation (outcome in the causal analysis) using socio-economic and demographic covariates (observational data).

One or more embodiments include calculating the average treatment effect (ATE) on a group of "treated" people by averaging the difference in outcomes between the treated and untreated individuals.

In some instances, enriched results are generated with interactive visualization of pattern medication discontinuation under a subpopulation to provide end users (e.g. subject-matter experts) insights on discriminating patterns and their causal effect on discontinuation for further investigation and to support decision-making.

FIG. 9 shows a treatment calendar. The example shows a subject identified by person id with two types of event values on a monthly basis over 12 months identified by timestamp; the event values correspond to (episode and discontinuation reason).

Further comments will now be provided re extending PrefixSpan to analyze large-scale and noisy data for pattern discovery in treatment discontinuation. An exemplary approach for causal effect estimation of treatment episodes will then be discussed.

Data-driven Discriminatory Sequence Mining: Sequential pattern mining is a data mining technique that discovers frequent sub-sequences in a sequence database. Particularly, one or more embodiments use PrefixSpan, a projection-based, sequential pattern-growth approach for efficient mining of temporal patterns. In this approach, a sequence database is recursively projected onto a set of smaller projected databases, and sequential patterns are grown in each projected database by exploring locally frequent fragments only.

Begin by defining several notations for the treatment pattern mining problem. Definition 1: Let $B=\{e_1, e_2, \ldots, e_m\}$ be a set of all items, also called the item base; here, different types of treatment episodes. An itemset is a subset of items if $I \subseteq B$. A sequence is an ordered list of itemsets; here, a series of monthly ordered episodes from calendar data. A sequence $T=(t_1 \rightarrow t_2 \rightarrow \ldots \rightarrow t_n)$ with $\forall k 1 \leq k \leq n: t_k \subseteq B$.

Definition 2: Let $I \subseteq B$ be an itemset and T a sequence over B, the cover of $\overline{I}$ is defined as the set:

$$K_T(I) = k \in 1, \ldots, n | I \subseteq t_k \quad (1)$$

The cover of an itemset is the index set of sequences that contains all items in I.

Definition 3: The value $$\sigma_T = \frac{1}{n}|K_T(I)|$$

is called relative support of I. The support of I is the fraction of sequences that contain it.

Definition 4: Given the minimum support $\sigma_{min} \in \mathbb{R}, 0 < \sigma hd\ min \leq 1$, the set of frequent itemsets is defined as:

$$\Phi_T(\sigma_{min}) = I \subseteq B | \sigma_T(I) \geq \sigma_{min} \quad (2)$$

Definition 5: A sequence $s=(s_1, s_2, \ldots, s_n)$ matches a sequence $s'=(s'_1, s'_2, \ldots, s'_m)$ if there exists $j_1 < j_2 < \ldots < j_n$ such that $s_i = s'_{j_i}$; define this function as match(s, s').

One pertinent goal with sequence mining is to identify treatment uptake patterns that may be unique to one cohort of patients (e.g., patients that discontinued due to health concerns). Extracting such patterns cannot only shed insight that is invaluable to domain experts, but can also have predictive power—i.e., be able to predict that a discontinuation event may occur ink steps if a particular pattern is being observed. To identify such unique or "discriminatory" sequences, one or more embodiments extend the PrefixSpan algorithm in several ways.

First, given two classes (patients that discontinued due to health concerns and those that did not discontinue) of the problem, it is appropriate to look for differentiating sequences among them. However, each patient's medication uptake pattern is typically unique and no two random patients have the same journey. This is a significant problem as it is not appropriate to simply apply a split-apply-combine operation such as GROUPBY and examine the differences between the two classes. To address this issue, one or more embodiments extend PrefixSpan to mine for patterns that are different between the two classes of interest. There are two parameters that should be set, $\sigma_{min}$ (see Definition 4) and max len. The first expresses a threshold on how often a particular pattern occurs (in terms of the minimum percentage across all the sequences in a treatment calendar dataset). The patterns identified are sequential in nature and are sub-sequences of the treatment uptake patterns.

Second, one or more embodiments extend PrefixSpan reporting such that each pattern is tagged with various metrics. While these are familiar concepts in association rule mining, one or more embodiments slightly modify their definitions to mine sequences with discriminatory power. The pertinent metrics in one or more embodiments are: support left and right and Lift(T, left, right), as discussed above.

With these definitions, the problem of finding discriminatory patterns can be formalized as follows. Let $$p_s = \frac{Pr(\text{match}(s, S_1))}{Pr(\text{match}(s, S_2))},$$

where $S_1$ and $S_2$ are two collections of sequences (e.g., those that continue medication use vs. those that do not). Let $$d_s = \max\left(p_s, \frac{1}{p_s}\right)$$

denote the discriminatory power of sequence s with respect to the two collections of sequences $S_1$ and $S_2$, where a larger $d_s \geq s$ is a more powerful discriminator.

Given the two collections of sequences $S_1$ and $S_2$ learn as a collection of sequences $S(|S| << |S_1|, |S_2|)$ such that with $\forall_s \in S$, $d_s$ with respect to $S_1$ and $S_2$ is greater than a given threshold. Note that, as will be appreciated by the skilled artisan, given the teachings herein, pruneByDominance is a function to eliminate those patterns q that are obtained by augmenting an existing pattern p, where p is shorter or more general than q, and has a higher confidence of predicting a class than q. Algorithm 1 in FIG. 10 shows the pseudo-code for DSM.

One or more embodiments provide extensions comprising a powerful tool in mining patterns of interest because they provide comprehensive matching algorithms that are explainable (useful in customer care and other application domains as much as in healthcare).

Causal Effect Estimation for Discontinuation Reasons: The need for causal analysis is driven by the fact that prediction is insufficient to inform actionable variables for potential interventions. Using the approach discussed previously, discriminative sub-sequences were identified over thousands of patients. While the generated insights are a powerful step towards decision making for improved healthcare practices, it is believed that they are not enough to choose any meaningful intervention without complex domain expertise, since the correlations may be incidental, and also, the effect of such interventions is unknown.

Thus, one or more embodiments develop an approach to estimate the effect of an intervention on some outcome from observational data. In the context of healthcare, one or more embodiments determine what is causing treatment discontinuation. DSM techniques provide the discontinuation hypothesis; causal methods estimate the effect of factors on discontinuation. To address this problem, one or more embodiments assume that basic socio-economic and demographic variables as well as those related to medical background, health preferences, contained in EHR data can be used to estimate causality for discontinuation after adjusting for confounding.

For each causal analysis, one or more embodiments conduct a series of steps from the observational data obtained from each individual patient's records in the demographic and health data. In one or more embodiments, the aim is to estimate the causal effect of the use of $T_3$ on discontinuation for health concern reasons. The null hypothesis $H_0$ assumes that the average of the individual causal effects is 0. Define L to be the set of covariates for each individual in the dataset. The outcome Y is defined as whether or not a patient surveyed in the EHR reported "discontinuation for health concern reason" i.e., side effects, in the past year (12 months), in the survey. Create the treatment assignment A based on the use of injectable medicaments in the past year. Based on whether the longest consecutive method in the past 12 months was injectable medicaments or not, assign each individual to the treated or untreated group.

With that problem setup, use Inverse Probability Weighting (IPW) with stabilized weights to calculate the weighted population outcome for each subgroup stratified by treatment assignment. Calculate the treatment effect by subtracting the outcome of the untreated group from the treated group. Formally, the causal risk difference, referred to as the treatment effect, is defined as:

$$Pr[Y^{a=1}=1] - Pr[Y^{a=0}=1]$$

In the above, $Y^a$ is the counterfactual outcome variable Y observed under treatment a (one of the two possible values of A). A problem that arises in estimating causal effects from observational data is confounding. Confounders are variables that affect both the treatment assignment and the outcome; they introduce bias in estimating the causal effect if they are not adjusted for. IPW removes confounding by creating a pseudo-population where the dependence between the covariates L and the treatment A is removed. Mathematically:

$$Y^a \perp\!\!\!\perp A | L \text{ for } a$$

This pseudo-population is created by weighting each individual by the reciprocal of the probability of being assigned to her or his treatment, conditioned on his or her covariates. That is:

$$W^A = 1/f(a|L)$$

or $$SW^A = f(A)/f(A|L)$$

The above is for stabilized weights which use the marginal probability of treatment instead of 1 as the weight numerator. This quantity can be obtained parametrically by fitting a model for the probability of being treated. This model is introduced below in the experiments section as a propensity model.

Experiments

This section presents a set of experiments conducted to answer appropriate questions, by analyzing medication use and discontinuation from three different angles to provide a holistic view of the problem landscape to domain experts. Regarding "Q1"—what patients transition to when they discontinue or switch between treatment methods, medication transitions were studied; i.e. how long an individual continues to use a treatment option and what the individual transitions to when a method is discontinued. Consider also whether there are any recurrent sequences of medication use and discontinuation across countries (or other discrete regions) ("Q2")—one or more embodiments use the discriminatory sequence mining algorithm to mine frequent temporal patterns of treatment use across all countries. Lastly, consider whether it is possible to go beyond covariate analysis to establish a causal effect of particular treatment options for a specific discontinuation reason ("Q3")—one or more embodiments frame the temporal patterns found as a hypothesis to examine if there is a causal effect between the type of treatment use and its discontinuation by measuring the magnitude by which the discontinuation outcome is changed when there is a variation in the causal effect as seen in the observational data.

Experimental setup for Q1: Treatment Transitions

Probability distributions of treatment transitions: To provide an overview of treatment use across each country based on the calendar data, in our experiments, we estimated the probability distributions per each treatment type. To determine how long an individual stayed on a particular treatment before switching to other methods or discontinuing to non-use, we calculated the frequencies of consecutive months of use for each specific treatment per country.

Given I the itemset of type of episodes, $D_i$ the set of sequences of calendar data for the country i (see the table of FIG. 9 for exemplary calendar data), sub-sequences were extracted with one type of episode $j \in I-\{B, P, T, 0\}$. The length was then calculated for each sub-sequence, excluding episodes that do not correspond to a treatment method. As a result, obtain a set of vectors $$V_{ji}=(|T_1|,\ldots,|T_n|),$$

where $$j \in I \text{ and } i \in D|T_i|$$

is the length of each sub-sequence found for that treatment over all calendar data in $D_i$. In our experiments, we used the Kernel Density Estimation (KDE) algorithm (the skilled artisan will be familiar with same from David W Scott, Multivariate density estimation: theory, practice, and visualization, John Wiley & Sons, 2015, and, given the teachings herein, will be able to modify techniques therein to implement one or more embodiments) to estimate the probability density function applied to:

$$\{V_{ji}|j \in I-\{B,P,T,0\}\}.$$

Figure 11:
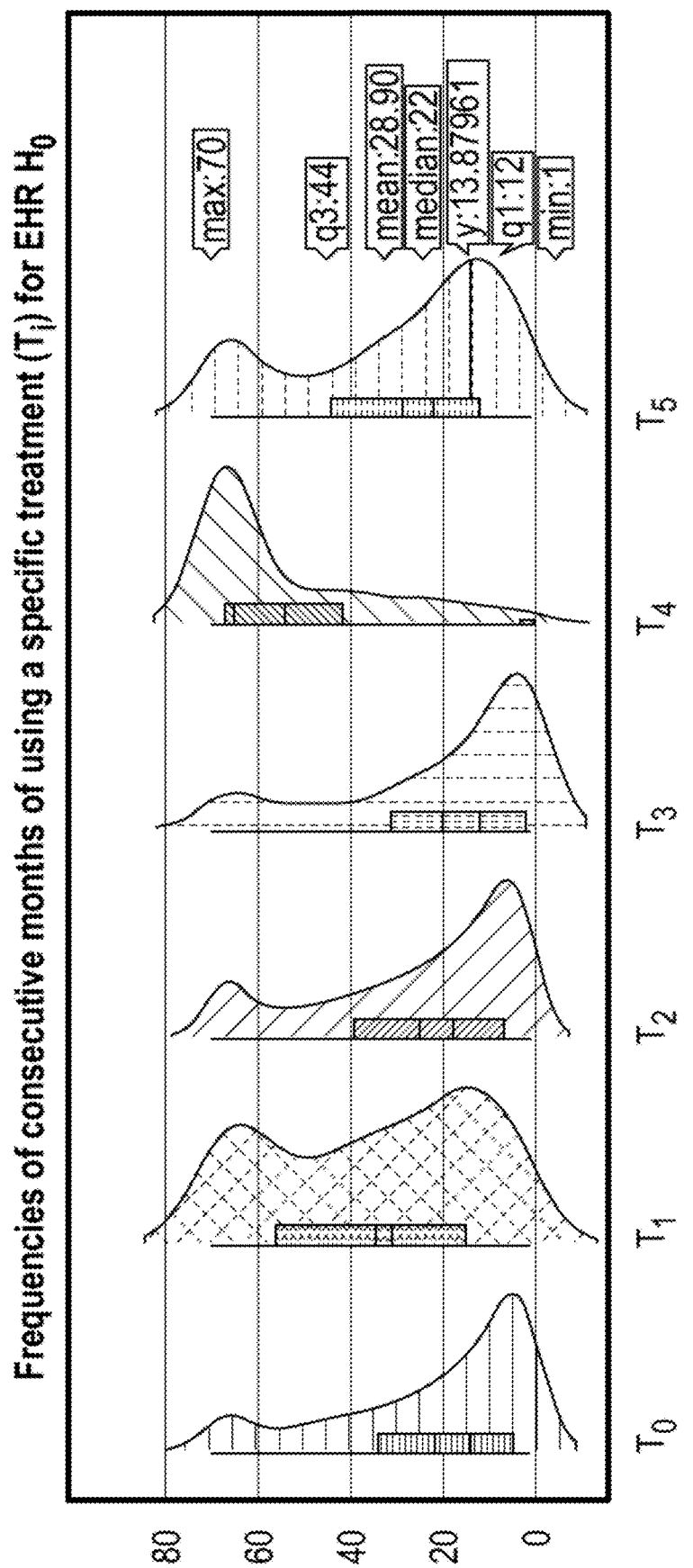
FIG. 11 shows exemplary violin plots produced using aspects of the invention.

FIG. 11 shows an example of interactive violin plots for frequencies of consecutive months of using a specific treatment Ti for EHR $H_0$ with six different treatment methods $T_0$, $T_1$, $T_2$, $T_3$, $T_4$, and $T_5$. This type of visualization gives the domain expert the tools to compare distributions across countries and treatments. In our experiments, we also estimated the probability of an individual adhering to a particular treatment for a number of months. Domain experts may find such analyses helpful to visualize the switching patterns; not just who discontinued treatment or why, but also some insight on what the type of behavior was (i.e., what type of treatment, if anything, the person used next). Further, the probability distribution of consecutive episodes may allow the experts to see and compare length of use in ways that show patterns not apparent from the usual "average months of use" that is commonly used in this domain.

Transitions between different types of episodes: In our experiments, after we studied the trends for consecutive months of use for each country, next we provided a simple one-to-one pattern transition. Using the sub-sequence already extracted as explained above, we formulated ordered pairs such as a set of tuples $P_k=(T_1, T_2), \ldots, (T_{n-1}, T_n))$, where $T_i$ is a sub-sequence of one type of treatment j with $j \in I$, $k \in D$ being a transition pair from each sub-sequence found to other treatment methods in $D_k$. Several examples of these transitions can be seen in FIGS. 12 and 13. In each Sankey plot, transitions from one type of episode can be observed; in this case, a $T_1$ and a $T_2$ episode, to all the other types of episodes. For patients that transition, the domain experts would like to know what they transition to, to better understand treatment uptake. In our experiments, we modeled these one-step transitions using a Sankey plot, wherein we selected the treatment of interest as the 'source' of the flow and plotted the amount of transition (indicated by the flow size) to all other 'destinations' i.e., treatment methods. The Sankey plots in FIGS. 12 and 13 illustrate the transitions from $T_1$ and $T_2$ in one exemplary country. Note that in our experiments, we repeated this analysis for five countries and summarize the results here for brevity.

Consider, for example, a treatment that tends to have high usage in all countries (e.g. top 5) but high rates of discontinuation, and this is of interest to domain experts. Analysis in accordance with one or more embodiments helps to support experts to design intervention methods to address discontinuation of such treatments.

Experimental setup for Q2: Discriminatory sub-sequence mining for fine-grained pattern insight Data Preprocessing: For sequence mining experiments, we processed over 95,855 treatment calendars corresponding to patient populations from several countries. The table of FIG. 9 shows an example used in the sequences analyses.

Retrospective reporting of medication use and discontinuation relies heavily on the ability of respondents to accurately recall events. To reduce recall bias, the 12 months prior to a discontinuation event were used in the analysis.

As described elsewhere herein, two parameters are employed to train the Discriminatory Sequence Model, namely, the time window to be analyzed (max len) and the minimal support required ($\sigma_{min}$). These parameters were tuned in consultation with domain experts, understanding that smaller minimal support within a time window provides more sequences that need to be examined for interpretation, and a shorter window provides short term insights. In our experiments, we set up a time window of max len=12 months to capture both long- and short-term treatment methods (which will vary depending on nature of the treatment and the condition being treated). For minimal support, we selected 0.3 as a minimum fraction of the population required for the patterns to be significant.

We determined two groups that would be evaluated in our experiments. For example, the table of FIG. 3 shows how we discriminated patterns of calendar data that contain discontinuations due to health concerns as opposed to the rest of the population. The reason for discontinuation is extracted from the discontinuation column. To evaluate each frequent pattern, we calculated support left, support right, and lift.

The results were discussed with the domain experts, and their comments and insights were added alongside when applicable.

Results: Results are shown in the table of FIG. 3, discussed elsewhere herein.

Additional discriminatory sub-sequence experiments with other reasons for discontinuation, particularly, health concerns, and others can be seen in the table of FIG. 14.

Experimental setup for Q3: Causal Analysis on Survey & Calendar Data

Data Preprocessing: In our experiments, we considered covariates from pertinent sections of an exemplary dataset, which contained potential confounders. In our experiments, we only selected covariates with at least 90% non-null values, and imputed null values with the median of the measured values for that covariate. Lastly, we one-hot encoded the categorical variables.

Models and hyper parameter setup: In our experiments, we used a calibrated logistic regression model to predict the treatment assignment which yields the propensity model for IPW. Calibration is important, as the true conditional probabilities of treatment are assumed when using propensity scores. In our experiments, we split the data into train and test sets, 70% and 30%, respectively, where the propensity model is trained on the test set and the causal effect is estimated on the train set. This mirrors what the "honest effect" done to reduce the bias of effect estimation due to model overfitting, as will be appreciated by the skilled artisan from, for example, Susan Athey and Guido Imbens, Recursive partitioning for heterogeneous causal effects, Proceedings of the National Academy of Sciences, 113(27): 7353-7360, 2016.

Causal Effect Estimation: Before estimating the causal effect we used a suite of diagnostic tools based on a known framework that employs known machine learning evaluation tools to fit the context of causal analysis and can help assess whether the causal effect can actually be identified, i.e., whether identifiability conditions are met. In our experiments, we assessed for violation of positivity, consistency, balanced covariates and accuracy of our propensity model. Given the teachings herein, the skilled artisan will be able to adopt certain known framework techniques such as those disclosed in Yishai Shimoni, Ehud Keeravani, Sivan Ravid, Peter Bak, Tan Hung Ng, Sharon Hensley Alford, Denise Meade, and Yaara Goldschmidt, An evaluation toolkit to guide model selection and cohort definition in causal inference, arXiv preprint arXiv:1906.00442, 2019. Further, the skilled artisan will be familiar with identifiability conditions to use, such as disclosed in Miguel A. Hernan and James M. Robins, Estimating causal effects from epidemiological data. Journal of Epidemiology & Community Health, 60(7): 578-586, 2006 ("Hernan et al.").

Figure 20:
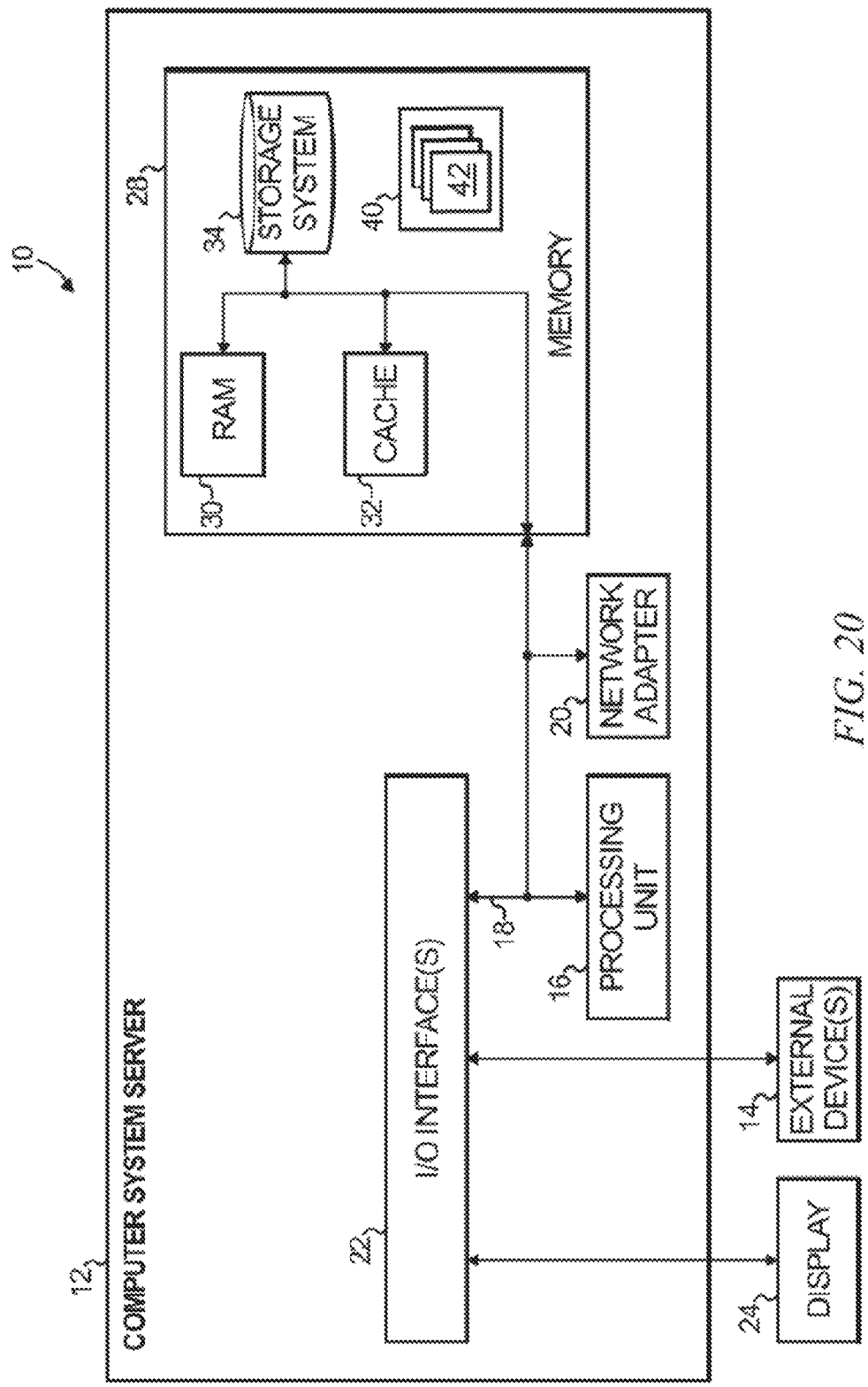
FIG. 20 depicts a computer system that may be useful in implementing one or more aspects and/or elements of the invention, also representative of a cloud computing node according to an embodiment of the present invention.

First, in our experiments, we assessed for potential violation of positivity i.e., that every individual has a greater than zero probability of being assigned to every treatment. We did this by visualizing the propensity distribution where a lack of common support or overlap between the two groups may indicate a violation. This implies that a particular subspace of covariates is populated solely by samples from one group and thus the counterfactual outcomes for these samples cannot be estimated. Views 2001 and 2004 in FIG. 20 show the propensity plots for first and second countries where there is common support between the two treatment groups. On the other hand, when it is observed that the propensity distribution for some countries do not overlap, this can be attributed, for example, to the high imbalance of treatment assignment for the corresponding datasets.

In our experiments, we proceeded with other diagnostics for only the aforementioned first and second countries with common support.

Secondly, the presence of one or more covariates that are highly discriminative between the two groups may also indicate a positivity violation and this will result in the propensity model having a very high ROC-AUC (area under the curve of the receiver operating characteristic). The propensity AUC for the first and second countries (EHR $H_0$ and EHR $H_3$) is shown in FIG. 15. A suitable value of the propensity AUC indicative of leading to reliable effect estimation is between 0.7 and 0.8. Refer, for example, to Yishai Shimoni, Ehud Karavani, Sivan Ravid, Peter Bak, Tan Hung Ng, Sharon Hensley Alford, Denise Meade, and Yaara Goldschmidt, An evaluation toolkit to guide model selection and cohort definition in causal inference, arXiv preprint arXiv:1906.00442, 2019; given the teachings herein, the skilled artisan will be able to adapt known techniques to select suitable values. We obtained an AUC of 0.77 for the first country and 0.73 for the second country. In addition to the Propensity AUC, we showed the Weighted-Propensity AUC obtained by reweighting the standard Receiver Operating Characteristic (ROC) curve using the weights drawn from the propensity model (i.e., by reweighting each unit with its IP-weight (reciprocal of the conditional probability of receiving the treatment that the unit is actually assigned)). This metric tests for consistency i.e., an individual with observed treatment A equal to a has an observed outcome Y equal to the individual's counterfactual outcome $Y^a$ and should be close to chance; the skilled artisan will be familiar with Hernan et al. in this regard.

Figure 16:
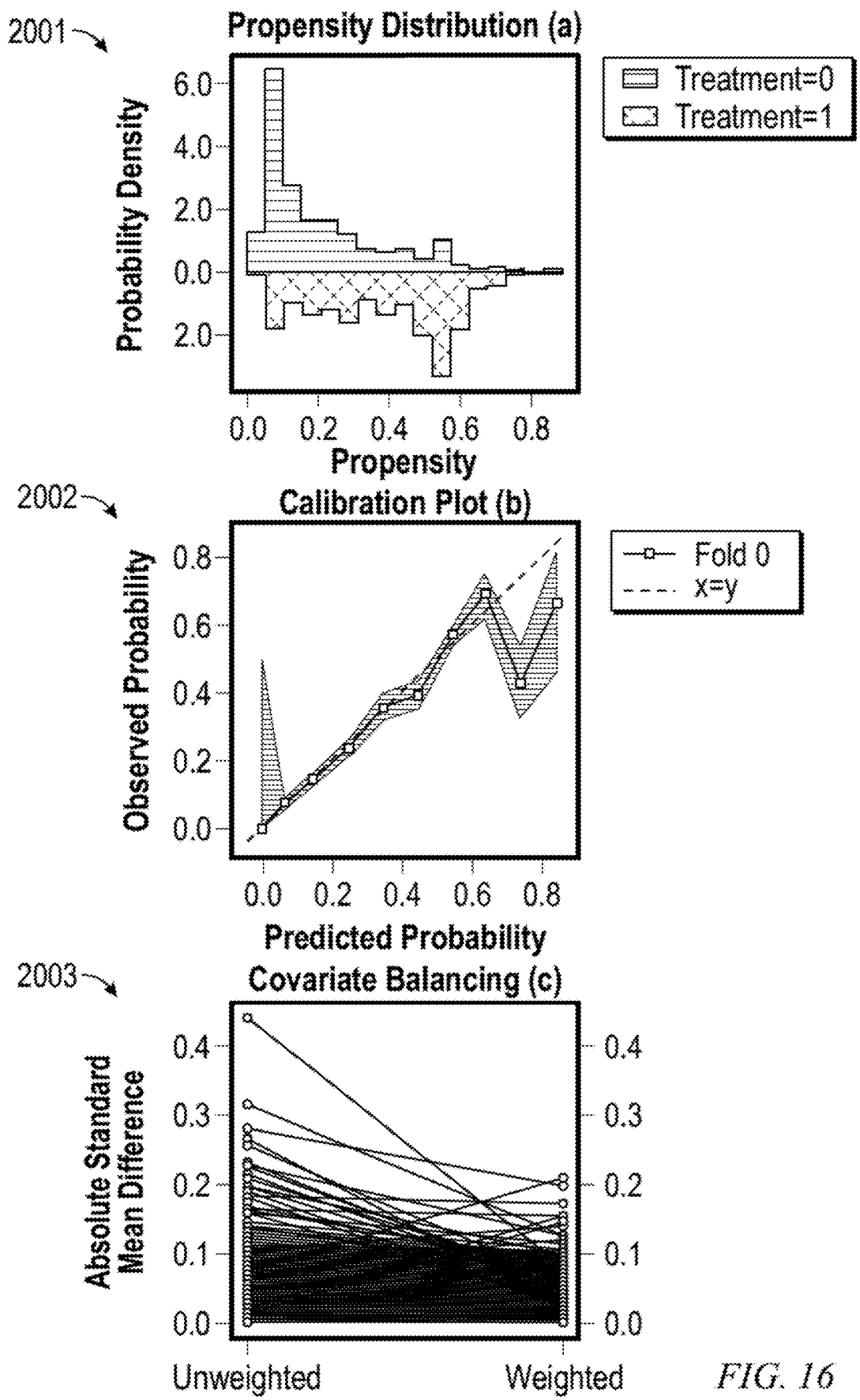
FIG. 16 shows exemplary propensity distributions, calibration plots, and covariate balancing, produced using aspects of the invention.
Figure 16:
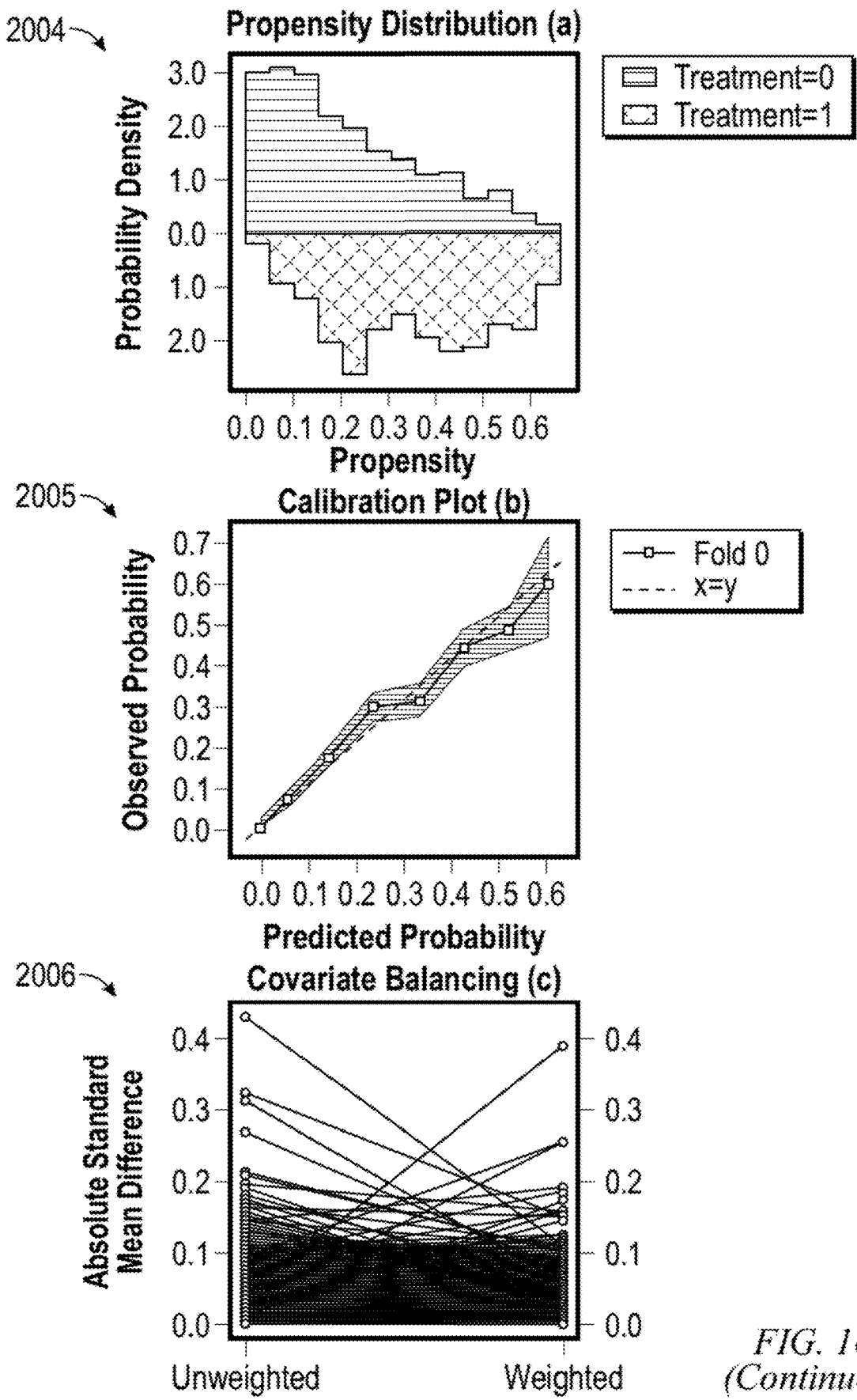

Furthermore, the propensity model is typically only accurate and useful if it captures the true probability that an individual is treated. An assessment can be made for overfitting, underfitting or model misspecification using a calibration plot. The calibration curves should be closer to the diagonal line. The calibration curves for the first and second country models are shown at 2002, 2005 in FIG. 16. Observe that the models mostly capture the true probability but get noisier where there are few data points at about P>0.6 for both models.

Lastly, marginal similarity between the covariate distributions of the two groups preempts selection bias and allows for marginal exchangeability; the skilled artisan will be familiar with Hernan et al. in this regard. This may be assessed using the standard mean difference (SMD) of the two distributions for all covariates and visualized with a covariate balancing plot. The covariate balancing plots for the first and second country models are shown at 2003, 2006 in FIG. 20. While there are several covariates that exhibit SMD values above the 0.1 threshold (a customary arbitrary threshold that assumes Gaussian distributions) recommended by the evaluation framework, note the high-dimension of the data and strong assumptions made about confounding variables as potential reasons for this.

Results: For both first and second countries (EHR $H_0$ and EHR $H_3$), the average treatment effect was calculated, and the table of FIG. 15 shows these as the percentage causal risk difference with 95% confidence intervals. In our experiments, we obtained the confidence interval by bootstrapping with 10000 samples. The results suggest that the use of certain treatment options does have a causal effect on discontinuation for health concern reasons, albeit to varying degrees, and thus the causal null hypothesis can be rejected here. This is of great importance to experts since a causal effect has been quantified, and based on the extent of causality policy makers can decide if and to what extent intervention is necessary.

We note that the lack of covariate overlap observed in some other countries can be characterized and removed from the data. Techniques such as removing samples beyond a cut-off point where there is no support between treated and untreated groups, identifying covariates that are highly unbalanced or dividing the covariate space into mutually exclusive regions with decision trees may be used.

Experimental Results Discussion

One or more embodiments employ Machine Learning and Big Data techniques to provide data-driven insights on treatment (e.g. medication) discontinuation. These insights can inform policy making to address unmet needs. One or more embodiments provide domain experts with the ability to visualize and compare frequency distributions of the different treatment methods and discontinuation flows across different methods, sub-populations, and countries. Using one or more embodiments, domain experts can derive insights such as the bimodal distribution of one or more treatment methods, and the before-after behavior of treatment uptake using the Sankey plots, even though the data was previously studied using prior art techniques. Further, analyzing the sequence of events in a medication uptake pattern and identifying which sequences lead to discontinuation, to what extent these sequences are discriminatory, and whether these sequences are common across sub-populations can help domain experts to further understand pertinent habits with respect to treatment.

A pertinent finding is that the results across DSM and causal analysis experiments reinforce each other. In the table of FIG. 3, in our experiments, we did not find discriminatory patterns for the use of injectable medicaments under the population that discontinue due to health concerns for the final row. Similarly, the estimated causal effect of injectable medicaments on discontinuation for health concerns for the same dataset is relatively small compared to the first row where the causal risk difference is larger (See the table of FIG. 15) and in our experiments, we found discriminatory patterns. Such agreement across techniques and their inherent explainability adds more confidence to the experts in trusting these results.

In another instance, the domain experts aimed to create a "super dataset" combining calendar data from multiple countries so as to perform a stratified DSM analysis such that there is sufficient sample size in rare classes. However, when we combined these datasets and ran our sequence mining methods, we did not mine any discriminatory patterns. This (negative) result has provided a very useful insight: blind merging of different datasets, with different years, countries, cultures, realities may not make sense. Due account should be taken of sub-populations that show some similarity in terms of their treatment uptake or other factors. The ability to carry out causal inference based on data-driven hypothesis means that the results can be directly mapped to interventions on the ground by program strategy teams.

One or more embodiments provide subject-matter experts with insights based on data-driven automatic sequence mining and causal analysis. The exemplary solution was tested across large datasets. One or more embodiments are able to provide decision support systems for policymakers regarding treatment and discontinuation for a given subpopulation. The ability to identify discriminative sub-sequences or predict discontinuation is immensely beneficial. One or more embodiments explore causal mechanisms and provide a more robust methodology for choosing interventions.

Techniques of the present invention can provide substantial beneficial technical effects. For example, one or more embodiments provide:

techniques for determining, predicting and/or estimating discontinuation of a course of medical treatment;
techniques for automatically generating a hypothesis for analyzing medication uptake behavior from calendar events using machine learning method;
techniques for intelligently analyzing and discovering causal-effect relationship of discontinuing a course of medical treatment;
efficient management of discontinuing of medical treatment on highly interactive interfaces; and/or techniques to modify a current course of treatment to proactively prevent it being inappropriately discontinued (e.g., if a current course of treatment, such as chemotherapy, causes nausea, administer an anti-nausea drug; if a current course of treatment has anxiety or insomnia as a side-effect, administer an anti-anxiety drug or sleep aid).

Given the discussion thus far, it will be appreciated that, in general terms, an exemplary method, according to an aspect of the invention, includes, with a trained, computerized discontinuation predictor machine learning component 1003, predicting, based on an input time series 1011, a time when a subject will discontinue a course of medical treatment; and, with a trained, computerized pattern behavior extractor machine learning component 1005, extracting from said input time series a top k discriminatory sequences via discriminatory sub-sequence mining. Said top k discriminatory sequences differentiate between first and second classes of interest to provide a hypothesis for downstream analysis of a cause of discontinuing said course of medical treatment. The method further includes, with a trained, causal effect estimator computerized machine learning component 1007, determining a reason why said subject will discontinue said course of medical treatment, based on said top k discriminatory sequences and additional data (e.g., survey data—in general, appropriate data from one or more data sources); and, with a computerized user interface 1009, providing said time when said subject will discontinue said course of medical treatment and said reason why said subject will discontinue said course of medical treatment to a responsible party (e.g., doctor, nurse, health aide, family member) to initiate an intervention.

One or more embodiments further include carrying out said intervention (e.g. using a computerized initiator and/or by the responsible party and/or someone under the responsible party's direction based on the computerized data/ instructions/initiation). In some cases, said intervention comprises, for example, counseling said subject and continuing to administer said course of medical treatment to said subject. In other cases, said intervention comprises, for example, counseling said subject, ceasing said course of medical treatment to said subject, and administering an alternative course of medical treatment to said subject which is not subject to said reason. The alternative course could include, for example, a different medicine, or the same medicine plus something else to mitigate the reason for ceasing (e.g. anti-nausea drug if patient will cease because of nausea), or a different dose of the same medicine.

In one or more embodiments, said computerized discontinuation predictor machine learning component 1003 comprises a recurrent neural network, and said predicting, based on said input time series, when said subject will discontinue said course of medical treatment comprises applying said recurrent neural network. Said recurrent neural network comprises, for example, a long short-term memory, and applying said recurrent neural network then comprises applying said long short-term memory. Applying said long short-term memory comprises, for example, processing an input sequence of treatment episodes by recursively applying a transition function to an internal hidden state vector, including computing an activation of said hidden state vector at a given time step based on a current one of said treatment episodes and a hidden state for a time step previous to said given time step.

In one or more embodiments, said input time series 1011 includes a collection of sequences for continuing said course of medical treatment and a collection of sequences for discontinuing said course of medical treatment, and said discriminatory sub-sequence mining comprises (e.g. with extractor 1005) determining a support left value and a support right value based on said input collections of sequences, and said top k discriminatory sequences are extracted based on said support left value and said support right value. One or more such embodiments further include pruning to eliminate from said top k discriminatory sequences those patterns that are obtained by augmenting an existing pattern, where said existing pattern is at least one of shorter and more general than a corresponding one of said augmented patterns, and has a higher confidence of predicting a class than said corresponding one of said augmented patterns. Refer, for example, to the algorithm of FIG. 10.

In one or more embodiments, providing said time and said reason with said computerized user interface comprises displaying a combination of: a bar plot to show coverage of said collection of sequences for continuing said course of medical treatment and said collection of sequences for discontinuing said course of medical treatment; and a shaded graph plot to show said top k discriminatory sequences (3001A and 3001B along with the grayscale bar plot 3004). Refer to FIG. 19.

In some cases, determining said reason why said subject will discontinue said course of medical treatment comprises determining a treatment effect (e.g. with estimator 1007) by subtracting an outcome for an untreated group from an outcome for a treated group, and removing confounders by inverse probability weighting. One or more embodiments use Inverse Probability Weighting (IPW) with stabilized weights to calculate weighted population outcome for each subgroup stratified by treatment assignment; given the teachings herein, the skilled artisan can adopt known techniques to implement one or more embodiments—see, e.g., Paul R. Rosenbaum and Donald B. Rubin, Constructing a control group using multivariate matched sampling methods that incorporate the propensity score, The American Statistician, 1985 Feb. 1; 39(1):33-8.

In another aspect, a computer program product comprising one or more computer readable storage media (see, e.g., discussion of elements 34, 40 elsewhere herein) having stored thereon: first program instructions executable by a computer system (purely by way of example and not limitation, a server or server coupled to a client) to cause the computer system to predict, based on an input time series, a time when a subject will discontinue a course of medical treatment (e.g. trained, computerized discontinuation predictor machine learning component 1003). Also stored thereon are second program instructions executable by the computer system to cause the computer system to extract from said input time series a top k discriminatory sequences via discriminatory sub-sequence mining, wherein said top k discriminatory sequences differentiate between first and second classes of interest to provide a hypothesis for downstream analysis of a cause of discontinuing said course of medical treatment (e.g. trained, computerized pattern behavior extractor machine learning component 1005). In addition, stored thereon are third program instructions executable by the computer system to cause the computer system to determine a reason why said subject will discontinue said course of medical treatment, based on said top k discriminatory sequences and additional data (e.g., survey data—in general, appropriate data from one or more data sources) (an example of the third program instructions includes a trained, causal effect estimator computerized machine learning component 1007). Even further, stored thereon are fourth program instructions executable by the computer system to cause the computer system to provide said time when said subject will discontinue said course of medical treatment and said reason why said subject will discontinue said course of medical treatment to a responsible party to initiate an intervention (e.g. computerized user interface 1009). Stated in an alternative manner, one or more embodiments include one or more non-transitory computer readable medium/media comprising computer executable instructions which when executed by a computer cause the computer to perform the method(s) described herein.

In another aspect, an exemplary system includes a memory (e.g. 30, discussed elsewhere); a non-transitory computer readable medium (e.g. 34, discussed elsewhere) including computer executable instructions; and at least one processor 16, coupled to the memory and the non-transitory computer readable medium, and operative to execute the instructions to be operative to perform any one, some, or all of the method steps described above. The instructions on the medium can also configure the processor to instantiate appropriate software components; for example, a trained, computerized discontinuation predictor machine learning component 1003, a trained, computerized pattern behavior extractor machine learning component 1005, a trained, causal effect estimator computerized machine learning component 1007, and a computerized user interface 1009. The methods, systems, and computer program products can also include the training of any one, some, or all of components 1003, 1005, 1007.

One or more embodiments of the invention, or elements thereof, can accordingly be implemented in the form of an apparatus/system including a memory and at least one processor that is coupled to the memory and operative to perform exemplary method steps. FIG. 20 depicts a computer system that may be useful in implementing one or more aspects and/or elements of the invention, also representative of a cloud computing node according to an embodiment of the present invention. Referring now to FIG. 20, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 20, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 20, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 20) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 1-2 and accompanying text. Consider, e.g., a cloud-based service 96 (or one or more elements thereof) to provide pattern discovery, prediction and causal effect estimation in treatment discontinuation and the like, located in layer 90.

It should be noted that any of the methods described herein can include an additional step of providing a system comprising distinct software modules (e.g. 42) embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described (e.g. 1003, 1005, 1007, 1009). The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI) 1009.

Exemplary System and Article of Manufacture Details

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    with a trained, computerized discontinuation predictor machine learning component, predicting, based on an input time series, a time when a subject will discontinue a course of medical treatment;
    with a trained, computerized pattern behavior extractor machine learning component, extracting from said input time series a top k discriminatory sequences via discriminatory sub-sequence mining by comparing two or more subgroups and performing mining in search of patterns that appear unequally in the two or more subgroups, wherein said top k discriminatory sequences differentiate between first and second classes of interest to provide a hypothesis for downstream analysis of a cause of discontinuing said course of medical treatment;
    with a trained, causal effect estimator computerized machine learning component, determining a reason why said subject will discontinue said course of medical treatment, based on said top k discriminatory sequences and additional data;
    with a computerized user interface, providing said time when said subject will discontinue said course of medical treatment and said reason why said subject will discontinue said course of medical treatment to a responsible party to initiate an intervention; and
    initiating said intervention to maintain said course of medical treatment.

2. The method of claim 1, further comprising carrying out said intervention.

3. The method of claim 2, wherein said intervention comprises counseling said subject and continuing to administer said course of medical treatment to said subject.

4. The method of claim 2, wherein said intervention comprises counseling said subject, ceasing said course of medical treatment to said subject, and administering an alternative course of medical treatment to said subject which is not subject to said reason.

5. The method of claim 1, wherein said computerized discontinuation predictor machine learning component comprises a recurrent neural network, and wherein said predicting, based on said input time series, when said subject will discontinue said course of medical treatment comprises applying said recurrent neural network.

6. The method of claim 5, wherein said recurrent neural network comprises a long short-term memory, and wherein applying said recurrent neural network comprises applying said long short-term memory.

7. The method of claim 6, wherein applying said long short-term memory comprises processing an input sequence of treatment episodes by recursively applying a transition function to an internal hidden state vector, including computing an activation of said hidden state vector at a given time step based on a current one of said treatment episodes and a hidden state for a time step previous to said given time step.

8. The method of claim 1, wherein:
    said input time series include a collection of sequences for continuing said course of medical treatment and a collection of sequences for discontinuing said course of medical treatment, and
    said discriminatory sub-sequence mining comprises determining a support left value and a support right value based on said input collections of sequences, and
    said top k discriminatory sequences are extracted based on said support left value and said support right value.

9. The method of claim 8, further comprising pruning to eliminate from said top k discriminatory sequences those patterns that are obtained by augmenting an existing pattern, where said existing pattern is at least one of shorter and more general than a corresponding one of said augmented patterns, and has a higher confidence of predicting a class than said corresponding one of said augmented patterns.

10. The method of claim 8, wherein providing said time and said reason with said computerized user interface comprises displaying a combination of:

a bar plot to show coverage of said collection of sequences for continuing said course of medical treatment and said collection of sequences for discontinuing said course of medical treatment; and a shaded scatter plot to show said top k discriminatory sequences.

11. The method of claim 1, wherein determining said reason why said subject will discontinue said course of medical treatment comprises determining a treatment effect by subtracting an outcome for an untreated group from an outcome for a treated group, and removing confounders by inverse probability weighting.

12. A computer program product comprising one or more computer readable storage media having stored thereon:

first program instructions executable by a computer system to cause the computer system to predict, based on an input time series, a time when a subject will discontinue a course of medical treatment;

second program instructions executable by the computer system to cause the computer system to extract from said input time series a top k discriminatory sequences via discriminatory sub-sequence mining by comparing two or more subgroups and performing mining in search of patterns that appear unequally in the two or more subgroups, wherein said top k discriminatory sequences differentiate between first and second classes of interest to provide a hypothesis for downstream analysis of a cause of discontinuing said course of medical treatment;

third program instructions executable by the computer system to cause the computer system to determine a reason why said subject will discontinue said course of medical treatment, based on said top k discriminatory sequences and additional data;

fourth program instructions executable by the computer system to cause the computer system to provide said time when said subject will discontinue said course of medical treatment and said reason why said subject will discontinue said course of medical treatment to a responsible party to initiate an intervention; and fifth program instructions executable by the computer system to cause the computer system initiate said intervention to maintain said course of medical treatment.

13. A system comprising:

a memory;

a non-transitory computer readable medium comprising computer executable instructions; and at least one processor, coupled to said memory and said non-transitory computer readable medium, and operative to execute said instructions to:

instantiate a trained, computerized discontinuation predictor machine learning component, a trained, computerized pattern behavior extractor machine learning component, a trained, causal effect estimator computerized machine learning component, and a computerized user interface;

with said trained, computerized discontinuation predictor machine learning component, predict, based on an input time series, a time when a subject will discontinue a course of medical treatment;

with said trained, computerized pattern behavior extractor machine learning component, extract from said input time series a top k discriminatory sequences via discriminatory sub-sequence mining by comparing two or more subgroups and performing mining in search of patterns that appear unequally in the two or more subgroups, wherein said top k discriminatory sequences differentiate between first and second classes of interest to provide a hypothesis for downstream analysis of a cause of discontinuing said course of medical treatment;

with said trained, causal effect estimator computerized machine learning component, determine a reason why said subject will discontinue said course of medical treatment, based on said top k discriminatory sequences and additional data;

with said computerized user interface, provide said time when said subject will discontinue said course of medical treatment and said reason why said subject will discontinue said course of medical treatment to a responsible party to initiate an intervention; and initiating said intervention to maintain said course of medical treatment.

14. The system of claim 13, wherein said computerized discontinuation predictor machine learning component comprises a recurrent neural network, applied to predict, based on said input time series, when said subject will discontinue said course of medical treatment.

15. The system of claim 14, wherein said recurrent neural network comprises a long short-term memory.

16. The system of claim 15, wherein said long short-term memory is applied by processing an input sequence of treatment episodes by recursively applying a transition function to an internal hidden state vector, including computing an activation of said hidden state vector at a given time step based on a current one of said treatment episodes and a hidden state for a time step previous to said given time step.

17. The system of claim 13, wherein:

said input time series include a collection of sequences for continuing said course of medical treatment and a collection of sequences for discontinuing said course of medical treatment, and said discriminatory sub-sequence mining comprises determining a support left value and a support right value based on said input collections of sequences, and said top k discriminatory sequences are extracted based on said support left value and said support right value.

18. The system of claim 17, wherein said trained, computerized pattern behavior extractor machine learning component is further operative to prune to eliminate from said top k discriminatory sequences those patterns that are obtained by augmenting an existing pattern, where said existing pattern is at least one of shorter and more general than a corresponding one of said augmented patterns, and has a higher confidence of predicting a class than said corresponding one of said augmented patterns.

19. The system of claim 17, wherein said computerized user interface provides said time and said reason by displaying a combination of:

a bar plot to show coverage of said collection of sequences for continuing said course of medical treatment and said collection of sequences for discontinuing said course of medical treatment; and a shaded graph plot to show said top k discriminatory sequences.

20. The system of claim 13, wherein said trained, causal effect estimator computerized machine learning component is operative to determine said reason why said subject will discontinue said course of medical treatment by determining a treatment effect by subtracting an outcome for an untreated group from an outcome for a treated group, and removing confounders by inverse probability weighting.

* * * * *